United States Patent
Endo et al.

(10) Patent No.: US 8,604,466 B2
(45) Date of Patent: Dec. 10, 2013

(54) ORGANIC ELECTROLUMINESCENT ELEMENT

(75) Inventors: Jun Endo, Chiba (JP); Chishio Hosokawa, Chiba (JP); Toshihiro Iwakuma, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 228 days.

(21) Appl. No.: 13/258,693

(22) PCT Filed: Mar. 23, 2010

(86) PCT No.: PCT/JP2010/055007
§ 371 (c)(1),
(2), (4) Date: Nov. 3, 2011

(87) PCT Pub. No.: WO2010/110277
PCT Pub. Date: Sep. 30, 2010

(65) Prior Publication Data
US 2012/0037895 A1    Feb. 16, 2012

(30) Foreign Application Priority Data
Mar. 24, 2009  (JP) .................................. 2009-072927

(51) Int. Cl.
*H01L 35/24* (2006.01)
(52) U.S. Cl.
USPC .................................... 257/40; 257/E51.001
(58) Field of Classification Search
USPC ............................................ 257/40, E51.001
See application file for complete search history.

(56) References Cited

U.S. PATENT DOCUMENTS

| 5,739,635 A | 4/1998 | Wakimoto |
| 2007/0170843 A1 | 7/2007 | Kawamura et al. |

FOREIGN PATENT DOCUMENTS

| JP | 9 17574 | 1/1997 |
| JP | 2002 367784 | 12/2002 |
| JP | 2005 251587 | 9/2005 |
| JP | 2005 259550 | 9/2005 |
| JP | 2006 222060 | 8/2006 |

OTHER PUBLICATIONS

International Search Report Issued Apr. 20, 2010 in PCT/JP10/055007 Filed Mar. 23, 2010.

*Primary Examiner* — Anthony Ho
(74) *Attorney, Agent, or Firm* — Oblon, Spivak, McClelland, Maier & Neustadt, L.L.P.

(57) ABSTRACT

Provided is an organic electroluminescence device that has solved the conventional problems, and is thermally and chemically stable, has high efficiency with which an electron is injected from a cathode layer or an intermediate conductive layer to a light emitting layer, provides high luminous efficiency at a low voltage, and can maintain a long lifetime. Specifically, the organic electroluminescence device is an organic electroluminescence device, including: two electrode layers and optionally one or more intermediate conductive layers; a light emitting layer between the electrode layers, or between one of the electrode layers and the intermediate conductive layer and/or between the intermediate conductive layers; and an electron injection region formed of one or two or more layers between the light emitting layer and the cathode layer and/or between the light emitting layer and the intermediate conductive layer, in which at least one layer in the electron injection region contains at least one kind selected from the group consisting of an oxide of a transition metal belonging to any one of Groups 5 to 8 of the periodic table, a nitrogen-containing heterocyclic derivative, and a chalcogenide, and further contains a compound represented by the formula: $M_xAO_y$ (in the formula, M represents Li, Na, K, Rb, or Cs, A represents Zr, V, Nb, Ta, Si, or Ge, x represents 1 or 2, and y represents an integer of 1 to 4).

19 Claims, No Drawings

ORGANIC ELECTROLUMINESCENT ELEMENT

TECHNICAL FIELD

The present invention relates to an organic electroluminescence device that is thermally and chemically stable, has high efficiency with which an electron is injected from a cathode layer or an intermediate conductive layer to a light emitting layer, and provides high luminous efficiency at a low voltage.

BACKGROUND ART

An organic electroluminescence device (hereinafter, "electroluminescence" may be abbreviated as "EL") is a spontaneous light emitting device which utilizes the principle that a fluorescent substance emits light by energy of recombination of holes injected from an anode layer and electrons injected from a cathode layer when an electric field is applied.

The organic EL device has a light emitting layer between the anode layer and the cathode layer, and an electron can be efficiently injected and transported by providing an electron injection region such as an electron injecting layer or an electron transporting layer between the light emitting layer and the cathode layer. A large number of researches have been heretofore conducted on the electron injection region with a view to improving the efficiency with which an electron is injected or transported and the heat resistance of the organic EL device. Given as a method of improving the efficiency with which an electron is injected or transported is, for example, a method involving using an extremely thin alkali metal oxide or alkali metal halide in the electron injecting layer (see Patent Literatures 1 and 2), a method involving using a co-deposited layer of a transition metal oxide and an alkali metal halide as the electron injecting layer (see Patent Literature 3), a method involving using the electron injecting layer containing a conductive metal oxide such as molybdenum oxide and an alkali metal (see Patent Literature 4), or a method involving laminating a transition metal oxide layer and an alkali metal or alkaline earth metal layer to provide the electron injecting layer (see Patent Literature 5).

CITATION LIST

Patent Literature

[PTL 1] JP 09-17574 A
[PTL 2] JP 2004-335468 A
[PTL 3] JP 2003-347059 A
[PTL 4] JP 2002-367784 A
[PTL 5] JP 2005-251587 A

SUMMARY OF INVENTION

Technical Problem

However, the methods disclosed in Patent Literatures 1 and 2 each involve the following problem. It is difficult to make the electron injecting layer formed of an alkali metal oxide or alkali metal halide thin in a uniform fashion over a large area, and the variations in thickness are responsible for variations in device characteristics. The methods each involve the following problem as well. Increasing the thickness of the electron injecting layer extremely raises the voltage at which the device is driven.

In the method disclosed in Patent Literature 3, a halogen in the electron injecting layer threatens to inhibit electron injection or to reduce a device lifetime. In the method disclosed in Patent Literature 4, the saturated vapor pressure of the alkali metal is so high that the metal may be liberated in a chamber to serve as a contaminant. In addition, the literature has no description concerning an effect of the use of an alkali metal compound to be used in the present invention.

In addition, investigations conducted by the inventors of the present invention have revealed that in the method disclosed in Patent Literature 5, an electron injection barrier between the electron transporting layer and the transition metal oxide layer is large and hence the efficiency with which an electron is injected from the cathode layer to the light emitting layer is insufficient.

Further, it is still hard to say that the methods each provide satisfactory luminous efficiency.

An object of the present invention is to provide an organic EL device that has solved the conventional problems, and is thermally and chemically stable, has high efficiency with which an electron is injected from a cathode layer or an intermediate conductive layer to a light emitting layer, provides high luminous efficiency at a low voltage, and can maintain a long lifetime as compared with a conventional organic EL device.

Solution to Problem

The inventors of the present invention have made extensive studies to achieve the object, and as a result, have found that an organic EL device that is thermally and chemically stable, has high efficiency with which an electron is injected from a cathode layer or an intermediate conductive layer to a light emitting layer, provides high luminous efficiency at a low voltage, and can maintain a long lifetime is obtained by co-depositing a compound represented by the following general formula (1) and a specific material in combination to form an electron injection region. Thus, the inventors have reached the present invention.

That is, the present invention provides an organic electroluminescence device, including: two electrode layers and optionally one or more intermediate conductive layers; a light emitting layer between the electrode layers, or between one of the electrode layers and the intermediate conductive layer and/or between the intermediate conductive layers; and an electron injection region formed of one or two or more layers between the light emitting layer and the cathode layer and/or between the light emitting layer and the intermediate conductive layer, in which at least one layer in the electron injection region contains at least one kind selected from the group consisting of an oxide of a transition metal belonging to any one of Groups 5 to 8 of the periodic table, a nitrogen-containing heterocyclic derivative, and a chalcogenide, and further contains a compound represented by the following general formula (1):

$$M_xAO_y \qquad (1)$$

where M represents Li, Na, K, Rb, or Cs, A represents Zr, V, Nb, Ta, Si, or Ge, x represents 1 or 2, and y represents an integer of 1 to 4.

Advantageous Effects of Invention

According to the present invention, there can be provided an organic EL device that is thermally and chemically stable, has high efficiency with which an electron is injected from a cathode layer or an intermediate conductive layer to a light emitting layer, and provides high luminous efficiency at a low voltage. In addition, a reduction in the lifetime of the organic EL device of the present invention can be suppressed because an electron can be efficiently injected into the light emitting layer of the device.

DESCRIPTION OF EMBODIMENTS (Organic EL Device)

An organic EL device of the present invention has a light emitting layer between two electrode layers (i.e., between an anode layer and a cathode layer; in a tandem type device, between an electrode layer and an intermediate conductive layer and/or between intermediate conductive layers when a plurality of intermediate conductive layers exist), and has an electron injection region between the light emitting layer and the cathode layer (between the light emitting layer and the intermediate conductive layer in the tandem type device) in ordinary cases.

It should be noted that the term "electron injection region" as used herein means such a region that an electron is injected from the cathode layer (the intermediate conductive layer in the tandem type device) to the light emitting layer, and refers to an electron injecting layer and an electron transporting layer.

The structure of the organic EL device is exemplified by laminates of "anode layer/light emitting layer/(electron transporting layer)/electron injecting layer/cathode layer," "anode layer/hole transporting layer/light emitting layer/(electron transporting layer)/electron injecting layer/cathode layer," "anode layer/hole injecting layer/hole transporting layer/light emitting layer/(electron transporting layer)/electron injecting layer/cathode layer," "anode layer/hole transporting layer/light emitting layer/hole blocking layer/(electron transporting layer)/electron injecting layer/cathode layer," "anode layer/hole injecting layer/hole transporting layer/light emitting layer/hole blocking layer/(electron transporting layer)/electron injecting layer/cathode layer," and the like, but is not particularly limited thereto.

The organic EL device of the present invention may be of any one of a bottom emission type, a top emission type, and a see-through type, or may even be a tandem type device having a tandem structure.

It should be noted that the term "tandem type device" refers to a device of such a structure that a plurality of light emitting units exist between the anode layer and the cathode layer, and the plurality of light emitting units are laminated in series through the intermediate conductive layer.

An example of the tandem structure is such a construction as described below, but is not particularly limited thereto. "Anode layer/hole injecting layer/hole transporting layer/first light emitting layer/electron transporting layer/electron injecting layer/intermediate conductive layer/hole injecting layer/hole transporting layer/second light emitting layer/electron transporting layer/electron injecting layer/cathode layer"

<Electron Injection Region>

The present invention has succeeded in obtaining an organic EL device that has improved efficiency with which an electron is injected from the cathode layer (the intermediate conductive layer in the tandem type device) to the light emitting layer (hereinafter simply referred to as "electron injection efficiency") and provides high luminous efficiency at a low voltage as described below. At least one layer in the electron injection region is formed of a layer (hereinafter referred to as "layer according to the present invention") containing at least one kind selected from the group consisting of an oxide of at least one kind of transition metal belonging to any one of Groups 5 to 8 of the periodic table, a nitrogen-containing heterocyclic derivative, and a chalcogenide, and further containing a compound represented by the following general formula (1) (hereinafter referred to as "compound (1)").

$$M_xAO_y \quad (1)$$

It should be noted that the "layer according to the present invention" is preferably formed by co-deposition.

The term "containing" in the above-mentioned expression "layer containing" means both the case where the layer is formed of the oxide of the transition metal belonging to any one of Groups 5 to 8 of the periodic table, the nitrogen-containing heterocyclic derivative, or the chalcogenide, and the compound (1), and the case where the layer contains any other component such as a metal or alloy having a small work function to be generally used as a cathode such as aluminum or an alloy of magnesium and silver, an electrically conductive compound, or a mixture thereof in addition to the oxide of the transition metal belonging to any one of Groups 5 to 8 of the periodic table, the nitrogen-containing heterocyclic derivative, or the chalcogenide, and the compound (1). It should be noted that the content of the other component is preferably 5 weight % or less with respect to all components that construct the "layer according to the present invention" from such a viewpoint that transparency is secured while an action of thermal reduction is expressed.

The phrase "at least one of electron injection regions" means that when a plurality of units of the tandem type device or the like can each have an electron injection region, at least one of the electron injection regions present in the respective units has only to be of the above-mentioned component construction.

Although the position at which the "layer according to the present invention" is present in the electron injection region is not particularly limited, the layer is preferably provided so as to contact an electrode layer (preferably the cathode layer) or the intermediate conductive layer from the viewpoint of the electron injection efficiency into the light emitting layer.

In the above-mentioned general formula (1), M represents lithium (Li), sodium (Na), potassium (K), rubidium (Rb), or cesium (Cs). Of those, M represents preferably Li or Na, more preferably Li from the viewpoint of luminous efficiency.

In addition, in the above-mentioned general formula (1), A represents a metal that is not an alkali metal or an alkaline earth metal, and represents zirconium (Zr), vanadium (V), niobium (Nb), tantalum (Ta), silicon (Si), or germanium (Ge) having poor conductive property. Of those, A preferably represents Si or Ge from the viewpoints of having a specific resistance of $10^{-2}$ Ω·cm or more and providing more satisfactory electron injection efficiency. It should be noted that A more preferably has a specific resistance of $10^0$ Ω·cm or more.

x represents 1 or 2 and y represents an integer of 1 to 4.

Examples of the compound (1) include $M_2ZrO_3$, $MVO_3$, $MNbO_3$, $MTaO_3$, $M_2SiO_3$, and $M_2GeO_3$ (M is as defined in the foregoing). Of those, $M_2SiO_3$ and $M_2GeO_3$ are preferred from the viewpoint of improving electron injection efficiency and luminous efficiency.

Specific examples of the compound (1) include lithium metasilicate, sodium metasilicate, potassium metasilicate, rubidium metasilicate, cesium metasilicate, lithium zirconate, lithium vanadate, lithium niobate, lithium tantalate, lithium germanate, and sodium germanate. Of those, lithium metasilicate and sodium metasilicate are preferred, and lithium metasilicate is more preferred from the viewpoints of electron injection efficiency and luminous efficiency.

The content of the compound (1) in the "layer according to the present invention" is preferably 5 to 90 weight %, more preferably 25 to 90 weight %, still more preferably 30 to 90 weight %, particularly preferably 40 to 85 weight % with respect to all components to be co-deposited. In particular, when the "layer according to the present invention" contains an oxide of at least one kind of transition metal belonging to any one of Groups 5 to 8 of the periodic table and the compound (1), the content of the compound (1) is preferably 5 to 90 weight % with respect to the total amount of both the oxide and the compound, and is more preferably 30 to 90 weight %, still more preferably 50 to 90 weight %, still further more preferably 65 to 90 weight %, particularly preferably 70 to 85 weight % from the viewpoints of improvements in electron injection efficiency and luminous efficiency. In addition, when the "layer according to the present invention" contains the nitrogen-containing heterocyclic derivative and the compound (1), the content of the compound (1) is preferably 5 to 90 weight % with respect to the total amount of both the derivative and the compound, and is more preferably 25 to 75 weight %, still more preferably 40 to 60 weight % from the viewpoints of the improvements in electron injection efficiency and luminous efficiency. In addition, when the "layer according to the present invention" contains the chalcogenide and the compound (1), the content of the compound (1) is preferably 5 to 90 weight % with respect to the total amount of both the chalcogenide and the compound, and is more preferably 25 to 75 weight %, still more preferably 40 to 60 weight % from the viewpoints of the improvements in electron injection efficiency and luminous efficiency.

(Electron Transportable Semiconductor)

As described in the foregoing, the "layer according to the present invention" contains at least one kind selected from the group consisting of, for example, an oxide of a transition metal belonging to any one of Groups 5 to 8 of the periodic table, a nitrogen-containing heterocyclic derivative, and a chalcogenide together with the compound (1). The oxide of the transition metal belonging to any one of Groups 5 to 8 of the periodic table, the nitrogen-containing heterocyclic derivative, and the chalcogenide are preferred because their electron mobilities are $10^{-6}$ cm$^2$/V·s or more. Hereinafter, the oxide of the transition metal belonging to any one of Groups 5 to 8 of the periodic table, the nitrogen-containing heterocyclic derivative, and the chalcogenide are described one by one.

(i) Oxide of Transition Metal Belonging to any One of Groups 5 to 8 of Periodic Table The incorporation of the oxide of the transition metal belonging to any one of Groups 5 to 8 of the periodic table into the "layer according to the present invention" can improve sputtering resistance, and can achieve an improvement in electron injection efficiency and high luminous efficiency at a low voltage.

Of the transition metals belonging to any one of Groups 5 to 8 of the periodic table, vanadium (V), niobium (Nb), tantalum (Ta), molybdenum (Mo), tungsten (W), rhenium (Re), and ruthenium (Ru) each having a semiconductor characteristic of a specific resistance of $10^0$ to $10^8$ Ω·cm are preferred, the transition metals belonging to Group 6 of the periodic table are more preferred, and Mo and W are still more preferred.

Specific examples of the oxide of a transition metal belonging to any one of Groups 5 to 8 of the periodic table include divanadium pentoxide ($V_2O_5$), divanadium tetraoxide ($V_2O_4$), divanadium trioxide ($V_2O_3$), vanadium dioxide ($VO_2$), vanadium oxide (VO), diniobium pentoxide ($Nb_2O_5$), niobium monoxide (NbO), tantalum pentoxide ($Ta_2O_5$), molybdenum dioxide ($MoO_2$), molybdenum trioxide ($MoO_3$), tungsten trioxide ($WO_3$), tungsten dioxide ($WO_2$), dirhenium heptoxide ($Re_2O_7$), rhenium oxide ($ReO_2$), diruthenium trioxide ($Ru_2O_3$), and ruthenium dioxide ($RuO_2$). Of those, divanadium pentoxide, diniobium pentoxide, molybdenum trioxide, tungsten trioxide, dirhenium heptoxide, rhenium oxide, and ruthenium dioxide are preferred, and molybdenum trioxide and tungsten trioxide are more preferred from the viewpoint of deposition property.

As the valence of a transition metal is apt to change, when a layer is formed by using a transition metal oxide as an electron injecting material, a composition ratio between the transition metal element and oxygen atom of the transition metal oxide may partly change at, for example, an interface with the light emitting layer owing to, for example, the desorption of oxygen during deposition. However, an organic EL device containing a transition metal oxide in such state is also included in the category of the present invention.

(ii) Nitrogen-Containing Heterocyclic Derivative

The incorporation of the nitrogen-containing heterocyclic derivative into the "layer according to the present invention" can improve film formability, and can achieve an improvement in electron injection efficiency and high luminous efficiency at a low voltage.

The nitrogen-containing heterocyclic derivative is not particularly limited as long as the derivative is a compound having a heterocyclic ring which contains a nitrogen atom, and exemplified by compounds having an imidazole ring, a triazole ring, a tetrazole ring, an oxadiazole ring, a thiadiazole ring, an oxatriazole ring, a thiatriazole ring, a benzoimidazole ring, a benzotriazole ring, a pyridinoimidazole ring, a pyrimidinoimidazole ring, or a pyridazinoimidazole ring. In particular, in the present invention, a benzoimidazole derivative represented by the following general formula (A) or (B) is preferred from the viewpoints of electron injection efficiency and luminous efficiency.

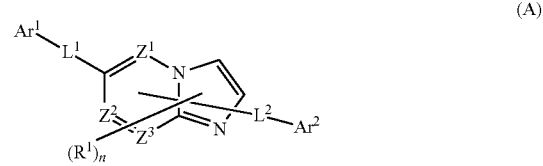

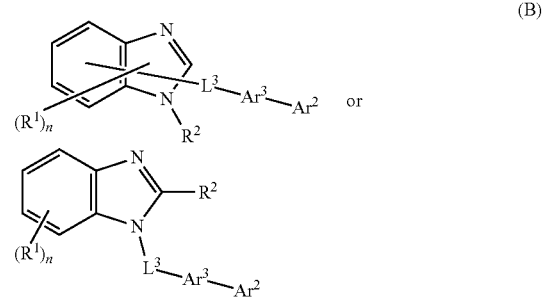

In the above-mentioned general formula: $Z^1$, $Z^2$, and $Z^3$ each independently represent a nitrogen atom or a carbon atom;

$R^1$ and $R^2$ each independently represent a substituted or unsubstituted aryl group having 6 to 60 carbon atoms, a substituted or unsubstituted heteroaryl group having 3 to 60 carbon atoms, an alkyl group having 1 to 20 carbon atoms, a halogen atom-substituted alkyl group having 1 to 20 carbon atoms, or an alkoxy group having 1 to 20 carbon atoms;

n represents an integer of 0 to 5, when n represents an integer of 2 or more, a plurality of $R^1$'s may be identical to or different from each other, and a plurality of $R^1$'s adjacent to each other may be bonded to each other to form a substituted or unsubstituted, aromatic hydrocarbon ring;

$Ar^1$ represents a substituted or unsubstituted aryl group having 6 to 60 carbon atoms or a substituted or unsubstituted heteroaryl group having 3 to 60 carbon atoms, and $Ar^2$ represents a hydrogen atom, an alkyl group having 1 to 20 carbon atoms, a halogen atom-substituted alkyl group having 1 to 20 carbon atoms, an alkoxy group having 1 to 20 carbon atoms, a substituted or unsubstituted aryl group having 6 to 60 carbon atoms, or a substituted or unsubstituted heteroaryl group having 3 to 60 carbon atoms, provided that any one of $Ar^1$ and $Ar^2$ represents a substituted or unsubstituted fused ring group having 10 to 60 carbon atoms or a substituted or unsubstituted, heterocyclic fused group having 9 to 60 ring forming atoms;

$Ar^3$ represents a substituted or unsubstituted arylene group having 6 to 60 carbon atoms or a substituted or unsubstituted heteroarylene group having 3 to 60 carbon atoms; and $L^1$, $L^2$, and $L^3$ each independently represent a single bond, a substituted or unsubstituted arylene group having 6 to 60 carbon atoms, a substituted or unsubstituted, heterocyclic fused group having 9 to 60 ring forming atoms, or a substituted or unsubstituted fluorenylene group.

Examples of the substituted or unsubstituted aryl group having 6 to 60 carbon atoms represented by $R^1$ or $R^2$ include a phenyl group, a naphthyl group, an anthryl group, a phenanthryl group, a naphthacenyl group, a chrysenyl group, a pyrenyl group, a biphenyl group, a terphenyl group, a tolyl group, a t-butylphenyl group, a (2-phenylpropyl)phenyl group, a fluoranthenyl group, a fluorenyl group, a monovalent group composed of spirobifluorene, a perfluorophenyl group, a perfluoronaphthyl group, a perfluoroanthryl group, a perfluorobiphenyl group, a monovalent group composed of 9-phenylanthracene, a monovalent group composed of 9-(1'-naphthyl)anthracene, a monovalent group composed of 9-(2'-naphthyl)anthracene, a monovalent group composed of 6-phenyl chrysene, and a monovalent group composed of 9-[4-(diphenylamino)phenyl]anthracene; a phenyl group, a naphthyl group, a biphenyl group, a terphenyl group, a 9-(10-phenyl) anthryl group, a 9-[10-(1'-naphthyl)]anthryl group, a 9-[10-(2'-naphthyl)]anthryl group, or the like is preferable. The aryl group is preferably an aryl group having 6 to 40 carbon atoms, or more preferably an aryl group having 6 to 20 carbon atoms.

Examples of the substituted or unsubstituted heteroaryl group having 3 to 60 carbon atoms represented by $R^1$ or $R^2$ include a pyrrolyl group, a furyl group, a thienyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, and a triazolyl group. The heteroaryl group is preferably a heteroaryl group having 3 to 40 carbon atoms, or more preferably a heteroaryl group having 3 to 20 carbon atoms.

The alkyl group having 1 to 20 carbon atoms represented by $R^1$ or $R^2$ may be any one of linear, branched, and cyclic alkyl groups, and examples thereof include a methyl group, an ethyl group, a propyl group, a butyl group, a pentyl group, and a hexyl group. The alkyl group is preferably an alkyl group having 1 to 10 carbon atoms, more preferably an alkyl group having 1 to 6 carbon atoms.

Examples of the halogen atom-substituted alkyl group having 1 to 20 carbon atoms represented by $R^1$ or $R^2$ include a trifluoromethyl group.

Examples of the alkoxy group having 1 to 20 carbon atoms represented by $R^1$ or $R^2$ include a methoxy group, an ethoxy group, a propoxy group, a butoxy group, a pentyloxy group, and a hexyloxy group. The alkoxy group is preferably an alkoxy group having 1 to 10 carbon atoms, more preferably an alkoxy group having 1 to 6 carbon atoms.

n represents preferably an integer of 0 to 2, more preferably 0 or 1.

Examples of the substituted or unsubstituted, aromatic hydrocarbon ring represented by the mutual bonding of the plurality of $R^1$'s adjacent to each other when n represents an integer of 2 or more include a benzene ring, a naphthalene ring, and an anthracene ring.

Examples of the substituted or unsubstituted aryl group having 6 to 60 carbon atoms and the substituted or unsubstituted heteroaryl group having 3 to 60 carbon atoms each represented by $Ar^1$ include the same ones as those given for $R^1$ and $R^2$, and preferred groups are also the same.

Examples of the alkyl group having 1 to 20 carbon atoms, the halogen atom-substituted alkyl group having 1 to 20 carbon atoms, the alkoxy group having 1 to 20 carbon atoms, the substituted or unsubstituted aryl group having 6 to 60 carbon atoms, and the substituted or unsubstituted heteroaryl group having 3 to 60 carbon atoms each represented by $Ar^2$ include the same ones as those given for $R^1$ and $R^2$, and preferred groups are also the same.

As described in the foregoing, one of $Ar^1$ and $Ar^2$ represents a substituted or unsubstituted fused ring group having 10 to 60 carbon atoms, or a substituted or unsubstituted, heterocyclic fused ring group having 9 to 60 atoms. Examples of the substituted or unsubstituted fused ring group having 10 to 60 carbon atoms include groups obtained by eliminating phenyl groups from the examples of the substituted or unsubstituted aryl group having 6 to 60 carbon atoms represented by $R^1$ or $R^2$ described in the foregoing. In addition, examples of the substituted or unsubstituted, heterocyclic fused ring group having 9 to 60 ring forming atoms include a quinolyl group, an isoquinolyl group, a benzofuryl group, and an imidazolyl group. Of those, a heterocyclic fused ring group having 9 to 14 ring forming atoms is preferred.

Examples of the substituted or unsubstituted arylene group having 6 to 60 carbon atoms and the substituted or unsubstituted heteroarylene group having 3 to 60 carbon atoms each represented by $Ar^3$ include the same ones as those given for $R^1$ and $R^2$, and preferred groups are also the same.

The substituted or unsubstituted arylene group having 6 to 60 carbon atoms represented by any one of $L^1$, $L^2$, and $L^3$ is preferably any one of those represented by the following formulae (101) to (110).

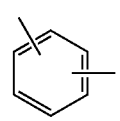

(101)

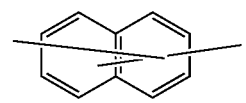

(102)

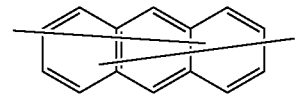

(103)

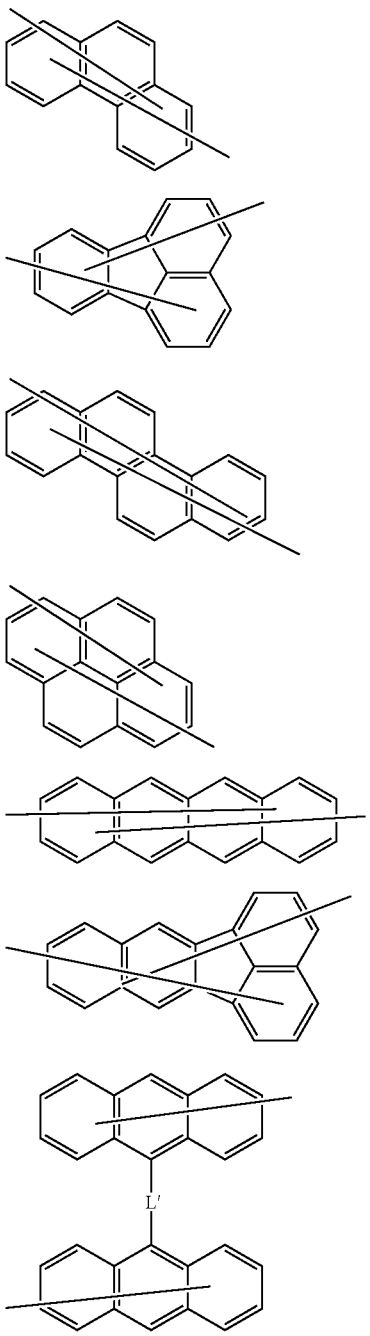

(104)

(105)

(106)

(107)

(108)

(109)

(110)

The arylene groups represented by the formulae (101) to (110) may each be substituted with a substituent. Examples of the substituent include a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. Examples of the halogen atom include a fluorine atom, a chlorine atom, a bromine atom, and an iodine atom. Examples of the substituted or unsubstituted aryloxy group having 6 to 40 carbon atoms include a methoxy group, an ethoxy group, an n-propoxy group, an isopropoxy group, an n-butoxy group, an s-butoxy group, and a t-butoxy group. Of those, an aryloxy group having 6 to 20 carbon atoms is preferred, and an aryloxy group having 6 to 10 carbon atoms is more preferred. Specific examples of each of the other substituents (the alkyl group, aryloxy group, aryl group, and heteroaryl group) include the same ones as those given in the foregoing.

In the formula (110), L' represents a single bond or a group selected from the group consisting of the following groups.

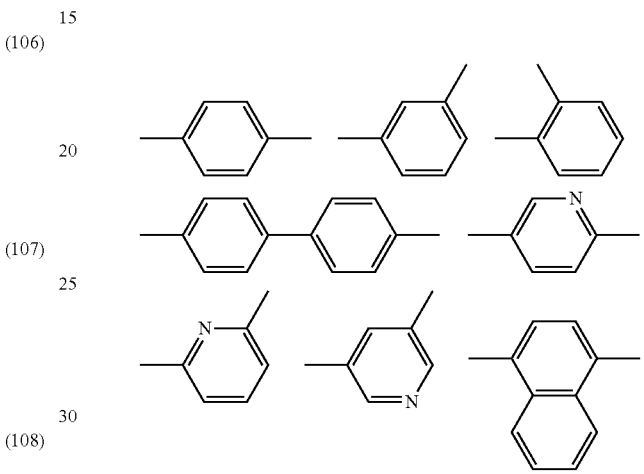

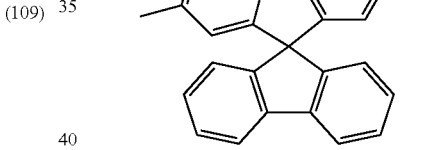

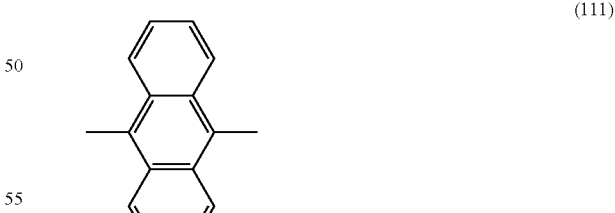

It should be noted that the formula (103) is more preferably a fused ring group represented by any one of the following formulae (111) to (125).

(111)

(112)

(113) 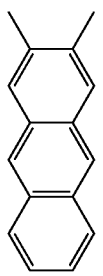
(114) 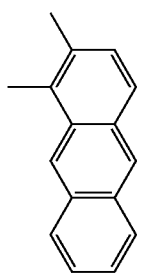
(115) 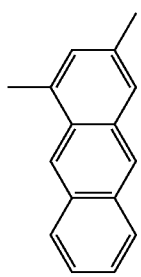
(116) 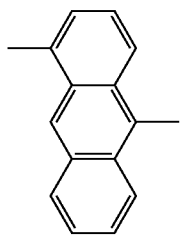
(117) 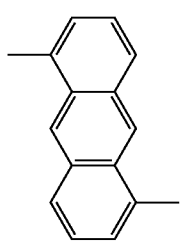
(118) 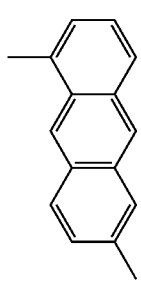
(119) 
(120) 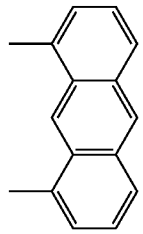
(121) 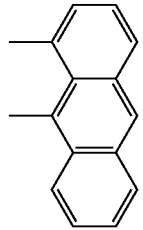
(122) 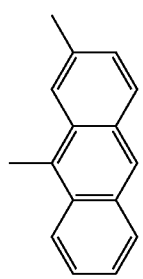
(123) 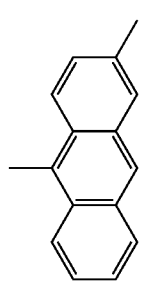
(124) 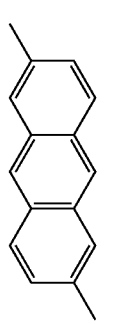

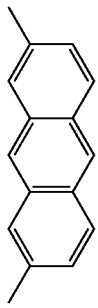

(125)

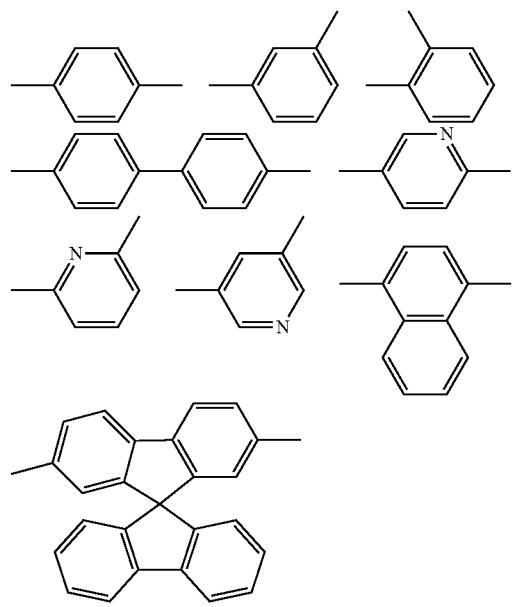

The arylene groups represented by the formulae (111) to (125) may each be substituted with a substituent such as a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. Specific examples of each of those substituents include the same ones as those given in the foregoing.

In addition, the heterocyclic fused group having 9 to 60 ring forming atoms represented by any one of $L^1$, $L^2$, and $L^3$ is preferably a heterocyclic fused group having 9 to 14 ring forming atoms, such as a pyridnylene group or a quinolinylene group. The heterocyclic fused groups may each be substituted with a substituent such as a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. Specific examples of each of those substituents include the same ones as those given in the foregoing.

It should be noted that $L^1$, $L^2$, and $L^3$ each independently represent preferably a group selected from the group consisting of the following formulae.

Examples of the substituent defined for each group in the general formulae (A) and (B) include a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms.

Examples of the halogen atom include fluorine, chlorine, bromine, and iodine.

Specific examples of the alkyl group having 1 to 20 carbon atoms, the alkoxy group having 1 to 20 carbon atoms, the aryloxy group having 6 to 40 carbon atoms, the aryl group having 6 to 40 carbon atoms, and the heteroaryl group having 3 to 40 carbon atoms include the same ones as those given in the foregoing.

Specific examples of benzoimidazole derivative represented by any one of the general formulae (A) and (B) are shown below. However, the present invention is not particularly limited to these examples.

| 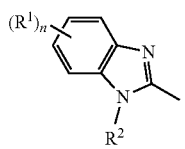 | $L^3$ | $Ar^3$ | $Ar^2$ |
|---|---|---|---|
| 1-1 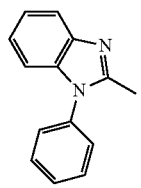 [SMILES: Cc1nc2ccccc2n1-c1ccccc1] | 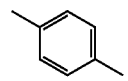 | 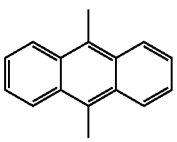 |  |

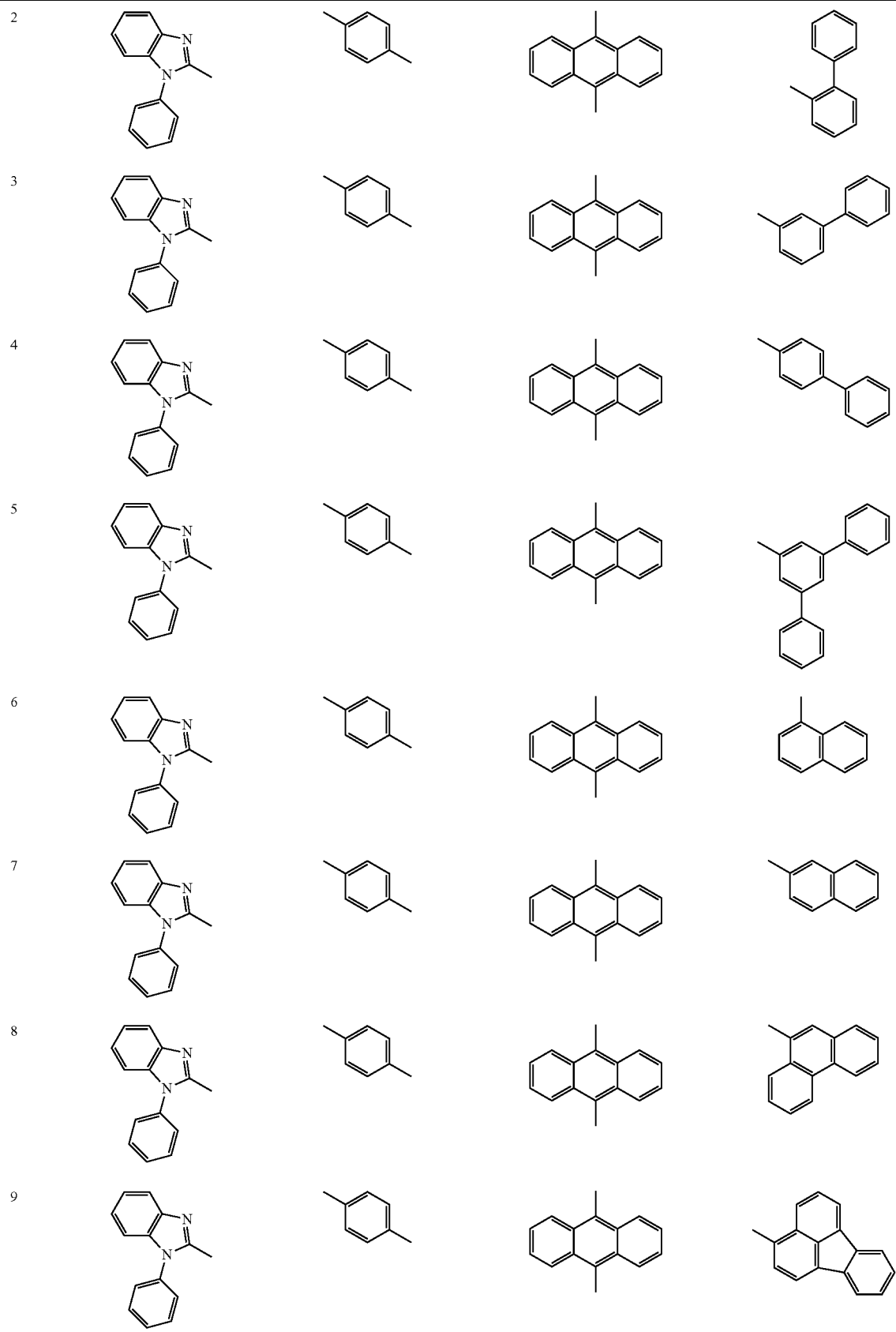

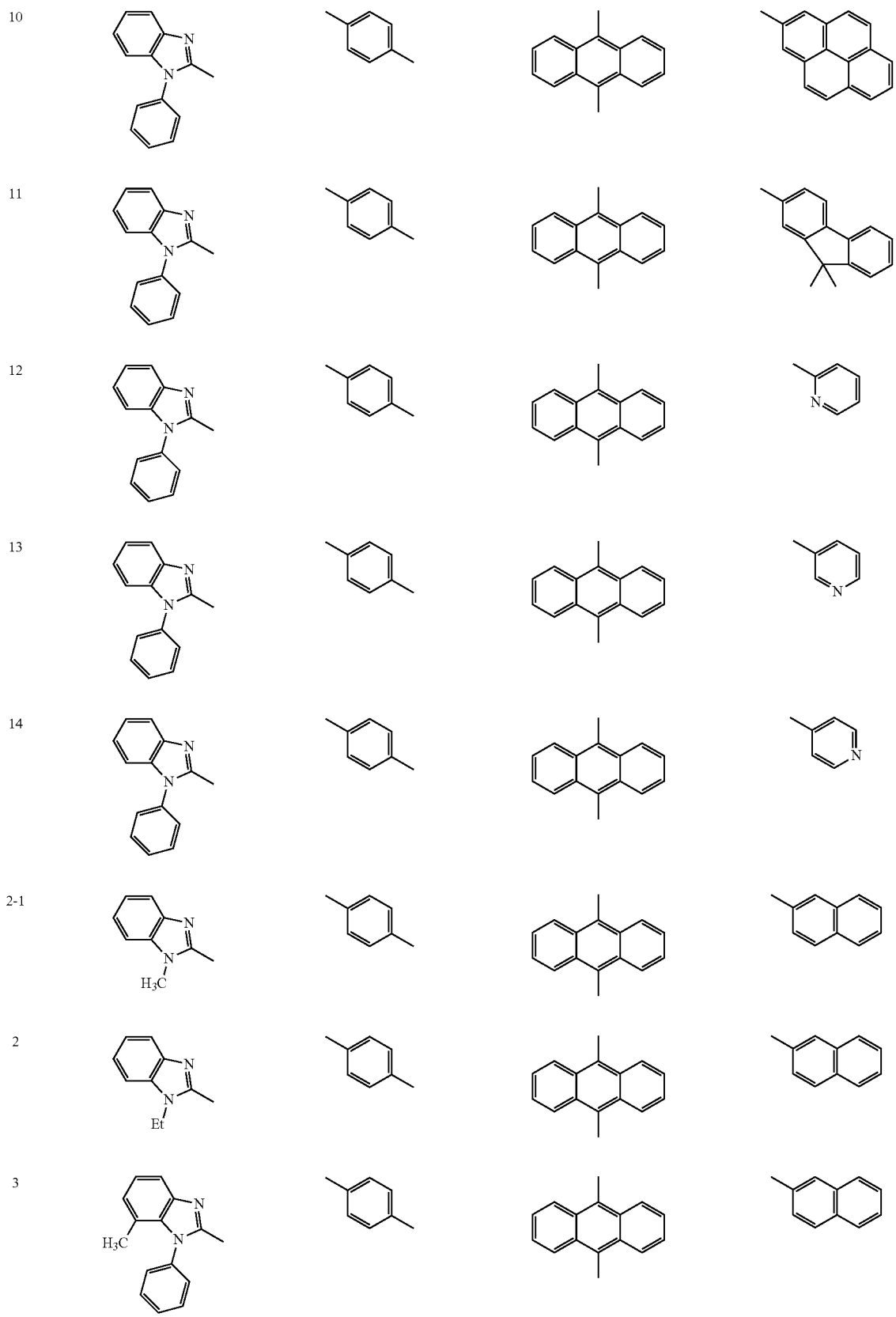

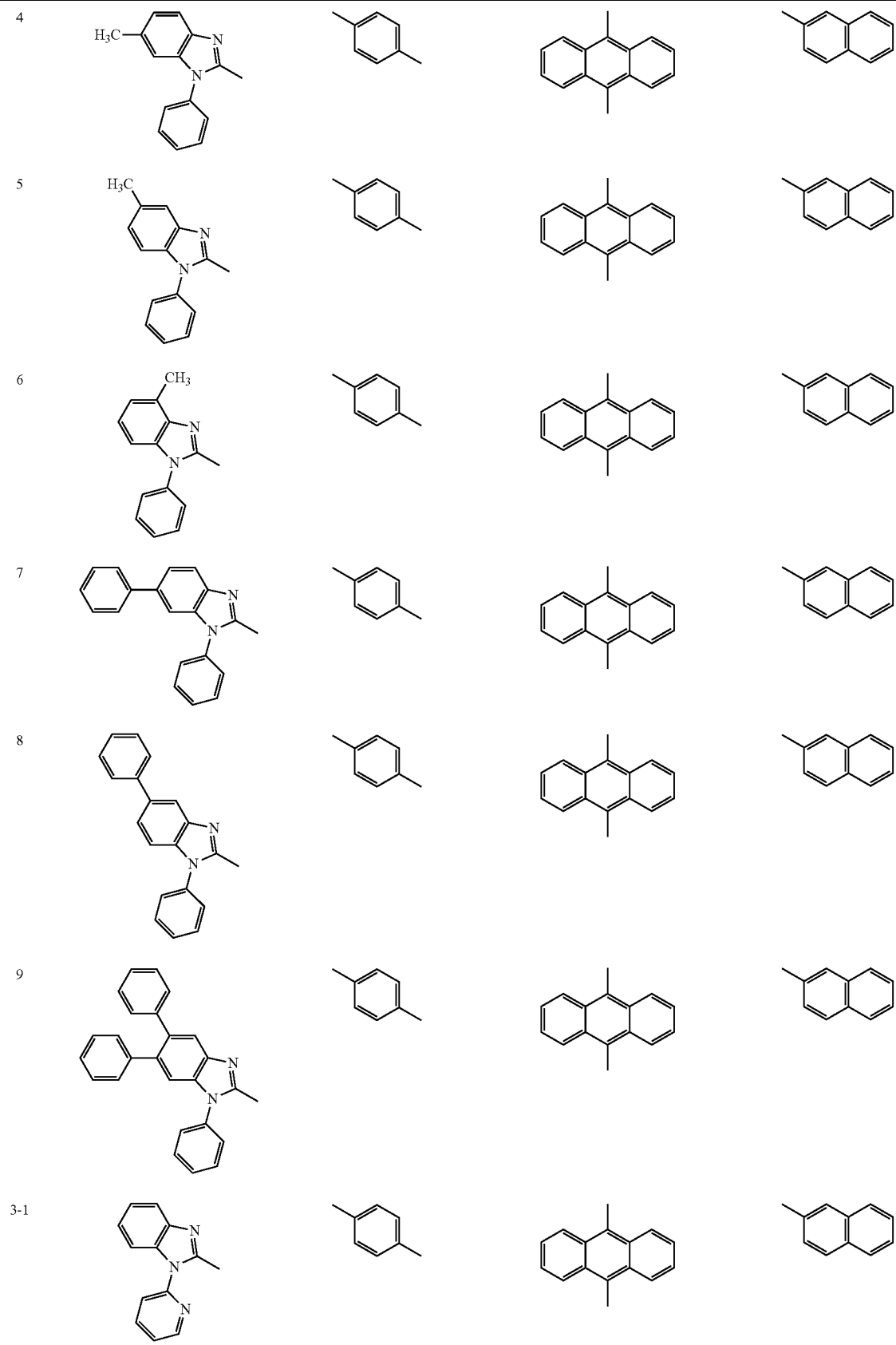

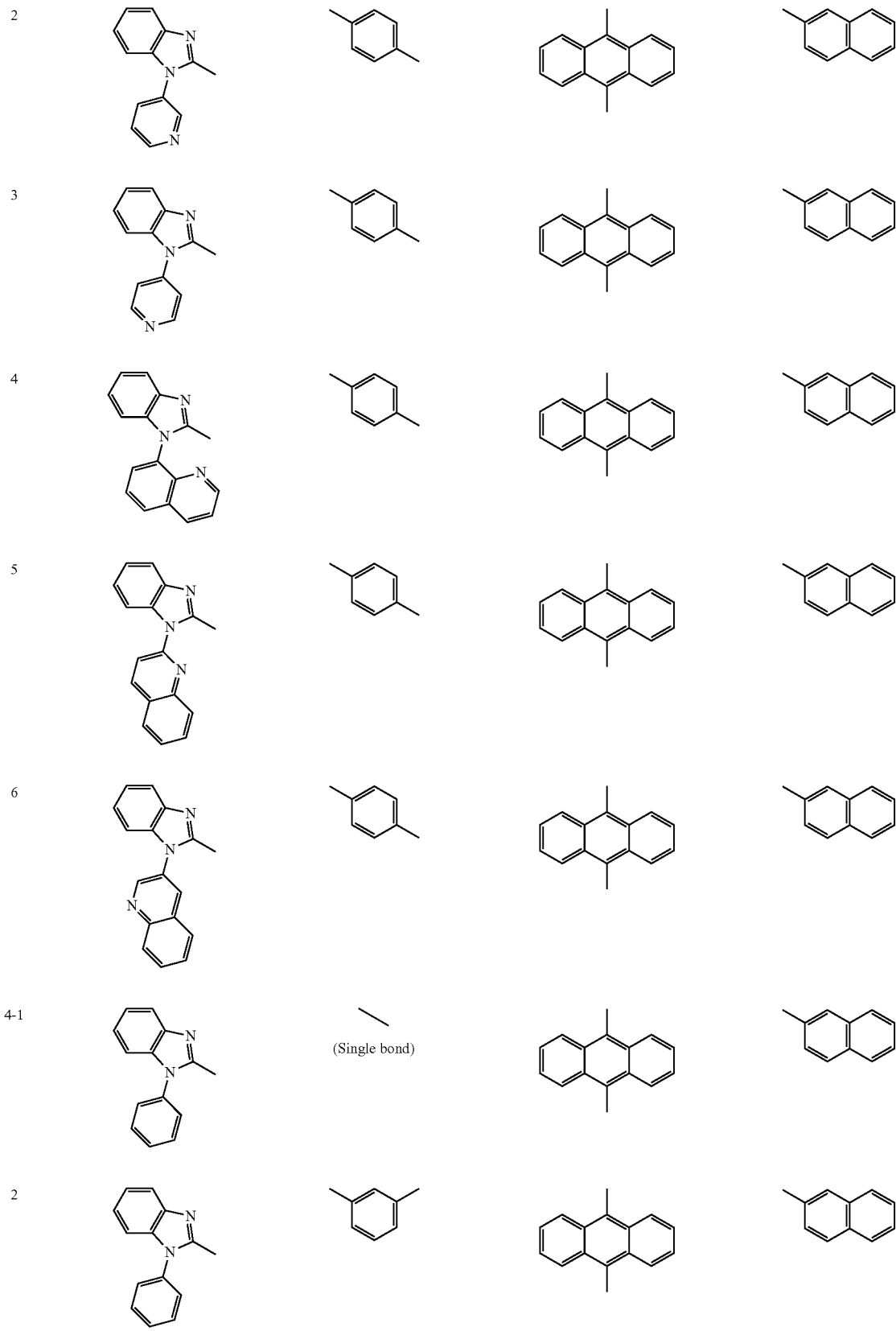

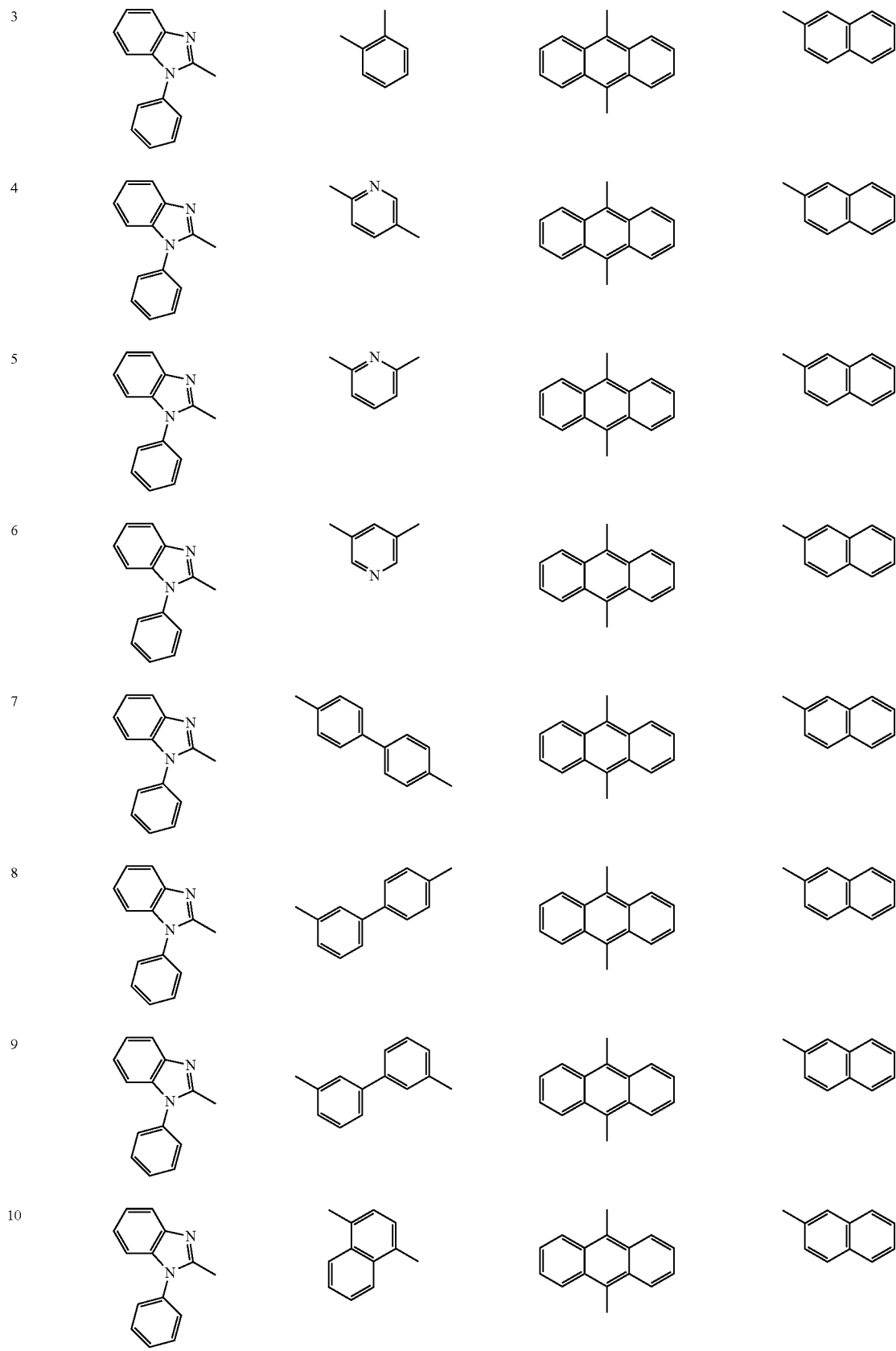

-continued
| | | | | |
|---|---|---|---|---|
| 11 | 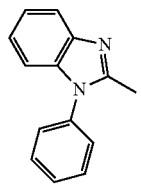 | 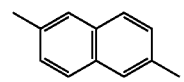 | 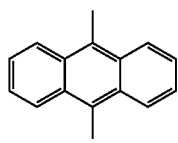 [SMILES: Cc1c2ccccc2c(C)c2ccccc12] | 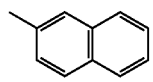 |
| 12 | 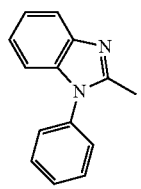 [SMILES: Cc1nc2ccccc2n1-c1ccccc1] | 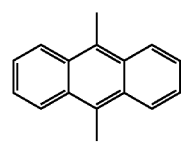 [SMILES: Cc1c2ccccc2c(C)c2ccccc12] | 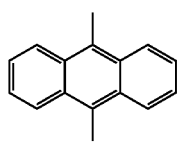 [SMILES: Cc1c2ccccc2c(C)c2ccccc12] | 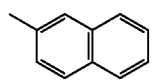 |
| 5-1 | 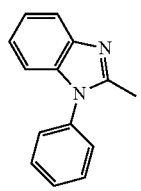 [SMILES: Cc1nc2ccccc2n1-c1ccccc1] | 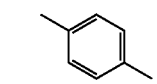 | 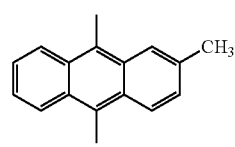 [SMILES: Cc1ccc2c(C)c3ccccc3c(C)c2c1] | 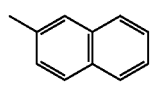 |
| 2 | 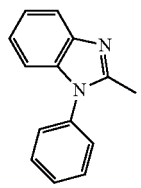 [SMILES: Cc1nc2ccccc2n1-c1ccccc1] | 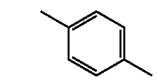 | 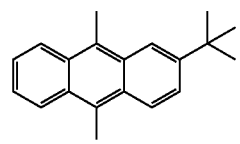 [SMILES: Cc1c2ccccc2c(C)c2cc(C(C)(C)C)ccc12] | 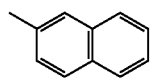 |
| 3 | 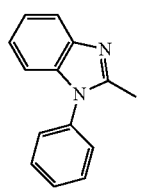 [SMILES: Cc1nc2ccccc2n1-c1ccccc1] | 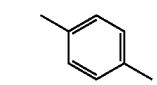 | 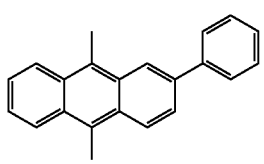 [SMILES: Cc1c2ccccc2c(C)c2cc(-c3ccccc3)ccc12] | 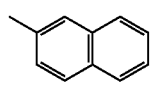 |
| 4 | 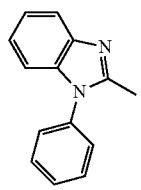 [SMILES: Cc1nc2ccccc2n1-c1ccccc1] | 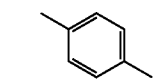 | 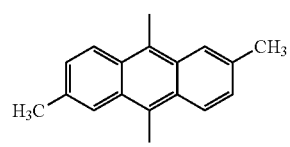 | 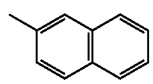 |
| 5 | 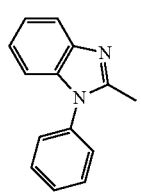 [SMILES: Cc1nc2ccccc2n1-c1ccccc1] | 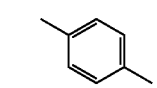 | 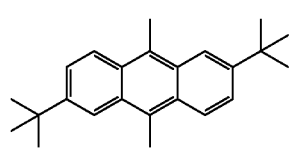 [SMILES: Cc1c2ccc(C(C)(C)C)cc2c(C)c2ccc(C(C)(C)C)cc12] | 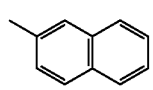 |
| 6 | 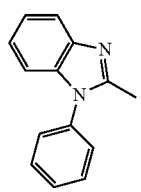 [SMILES: Cc1nc2ccccc2n1-c1ccccc1] | 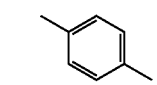 | 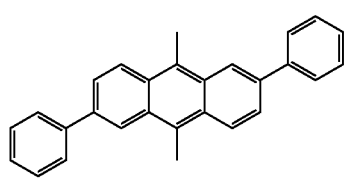 [SMILES: Cc1c2ccc(-c3ccccc3)cc2c(C)c2ccc(-c3ccccc3)cc12] | 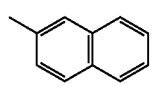 |

-continued
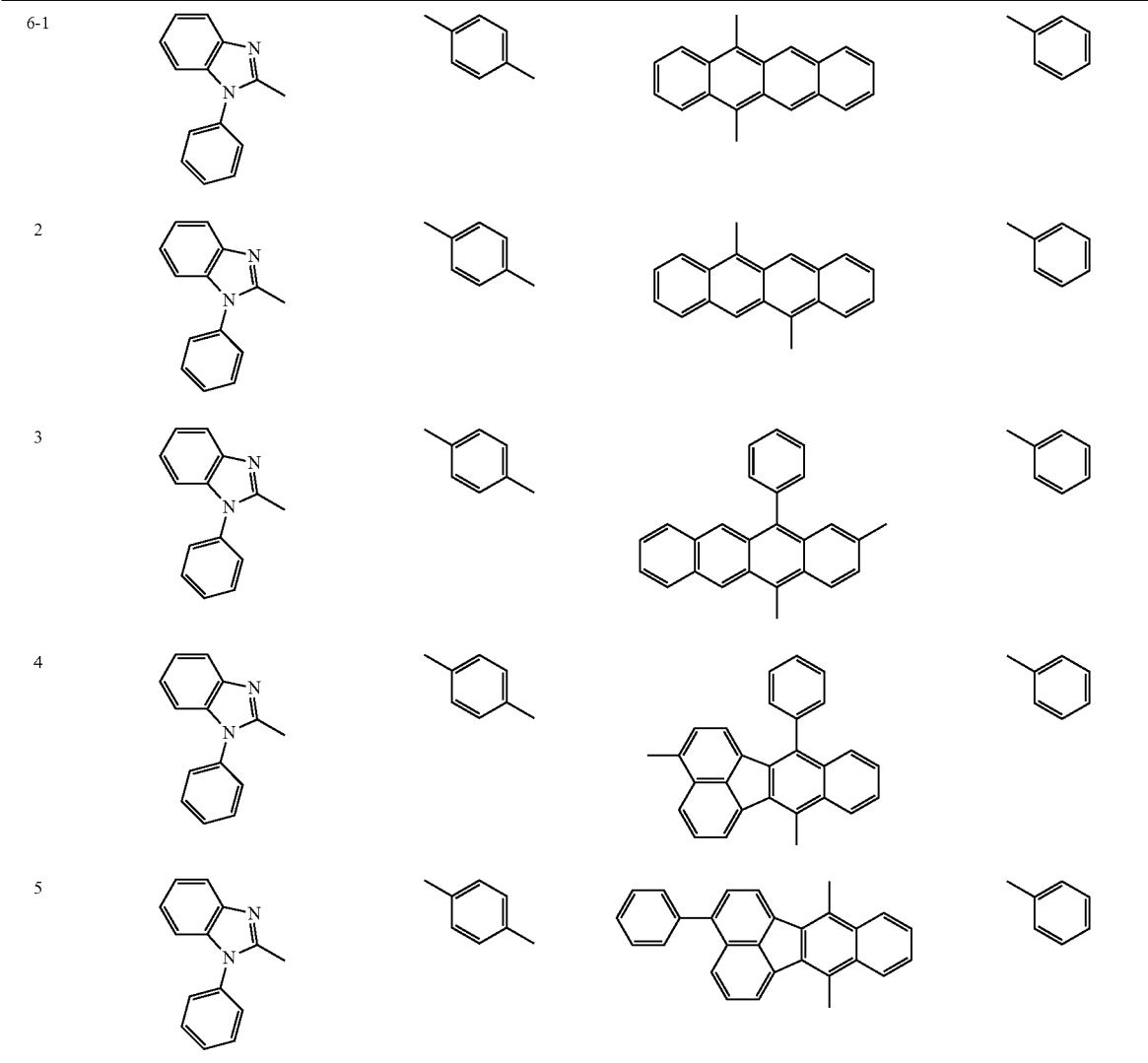
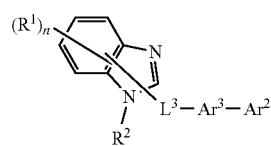 | $L^3$ | $Ar^3$ | $Ar^2$
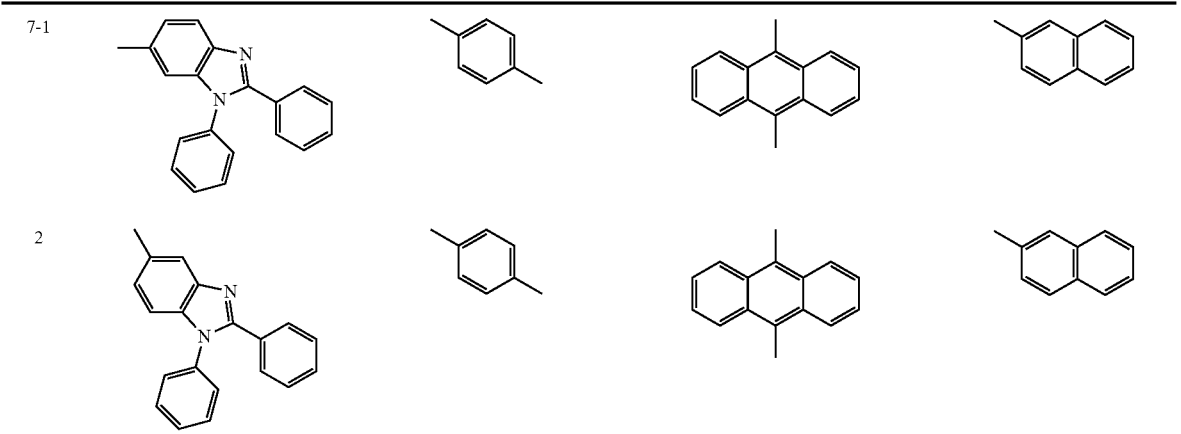

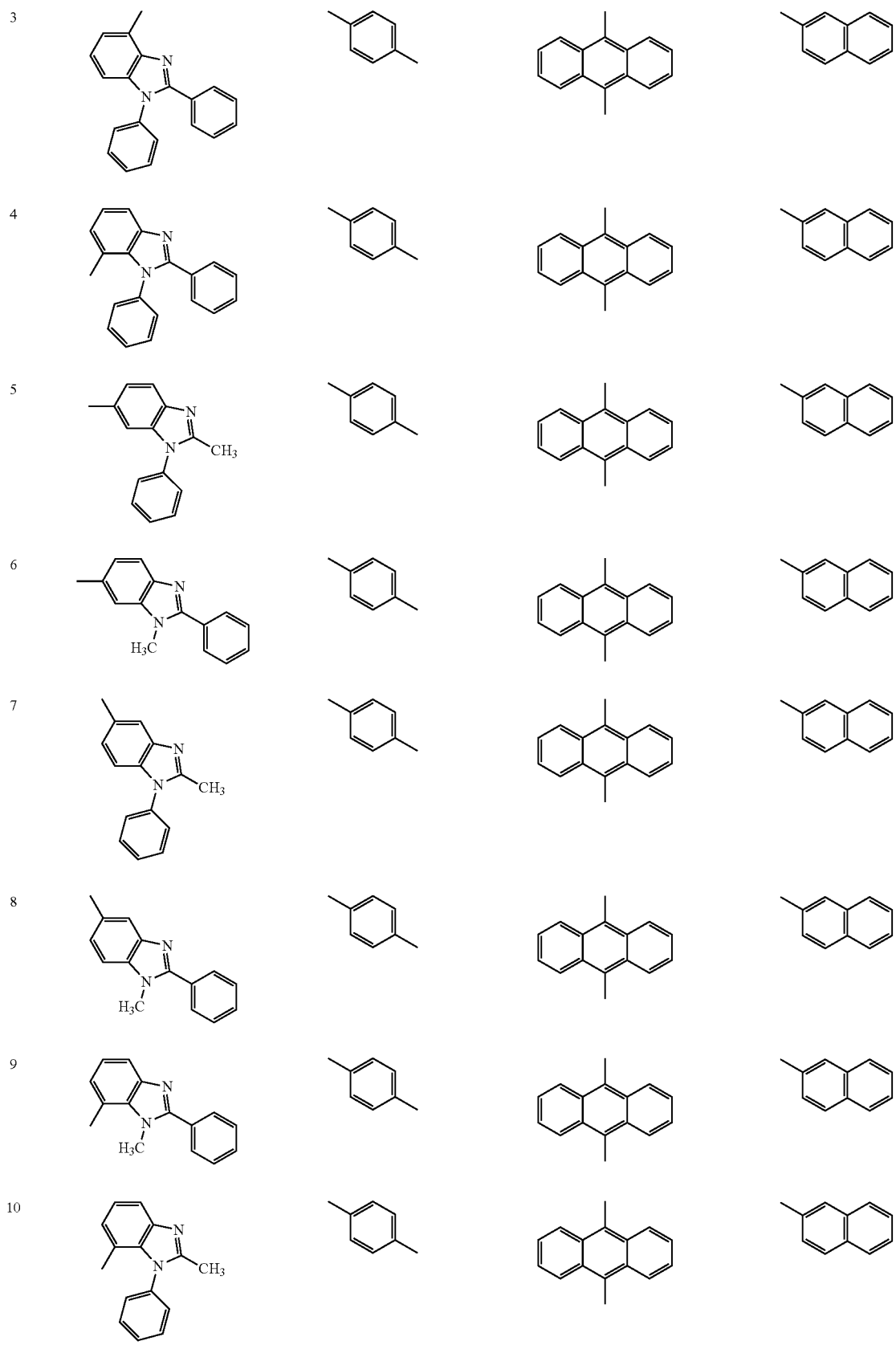

-continued

| | (R¹)ₙ-benzimidazole-R² | L³ | Ar³ | Ar² |
|---|---|---|---|---|
| 8-1 | 1-phenyl-2-methyl-benzimidazole | 1,4-phenylene | 1,4-phenylene | phenyl |
| 2 | 1-phenyl-2-methyl-benzimidazole | 1,4-phenylene | 1,3-phenylene | phenyl |
| 3 | 1-phenyl-2-methyl-benzimidazole | 1,4-phenylene | 1,4-naphthylene | phenyl |
| 4 | 1-phenyl-2-methyl-benzimidazole | 1,4-phenylene | 2,6-naphthylene | phenyl |
| 5 | 1-phenyl-2-methyl-benzimidazole | 1,4-phenylene | 9,10-phenanthrenylene | phenyl |
| 6 | 1-phenyl-2-methyl-benzimidazole | 1,4-phenylene | 2,7-phenanthrenylene | phenyl |
| 7 | 1-phenyl-2-methyl-benzimidazole | 1,4-phenylene | 9-phenanthrenyl | H |

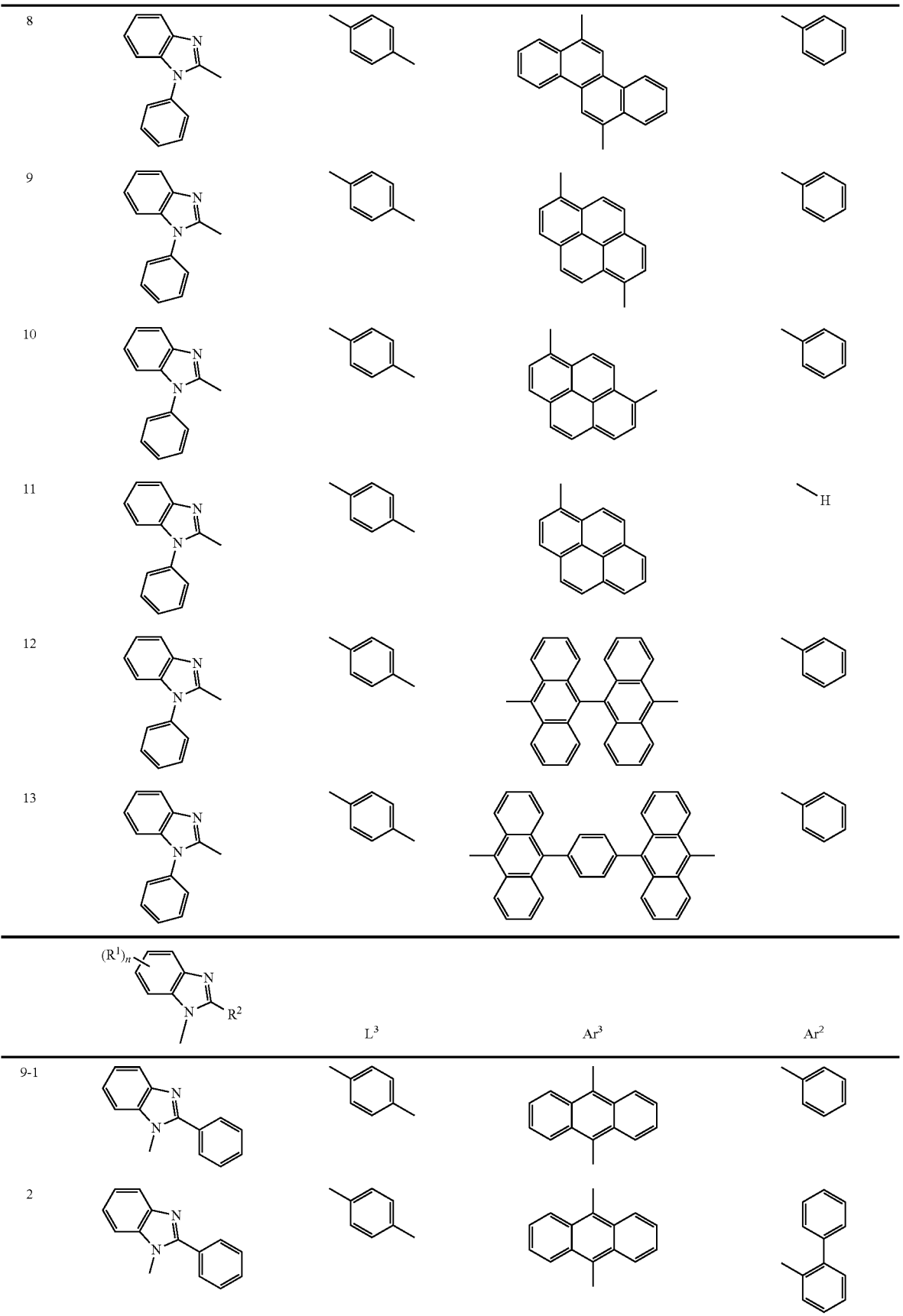

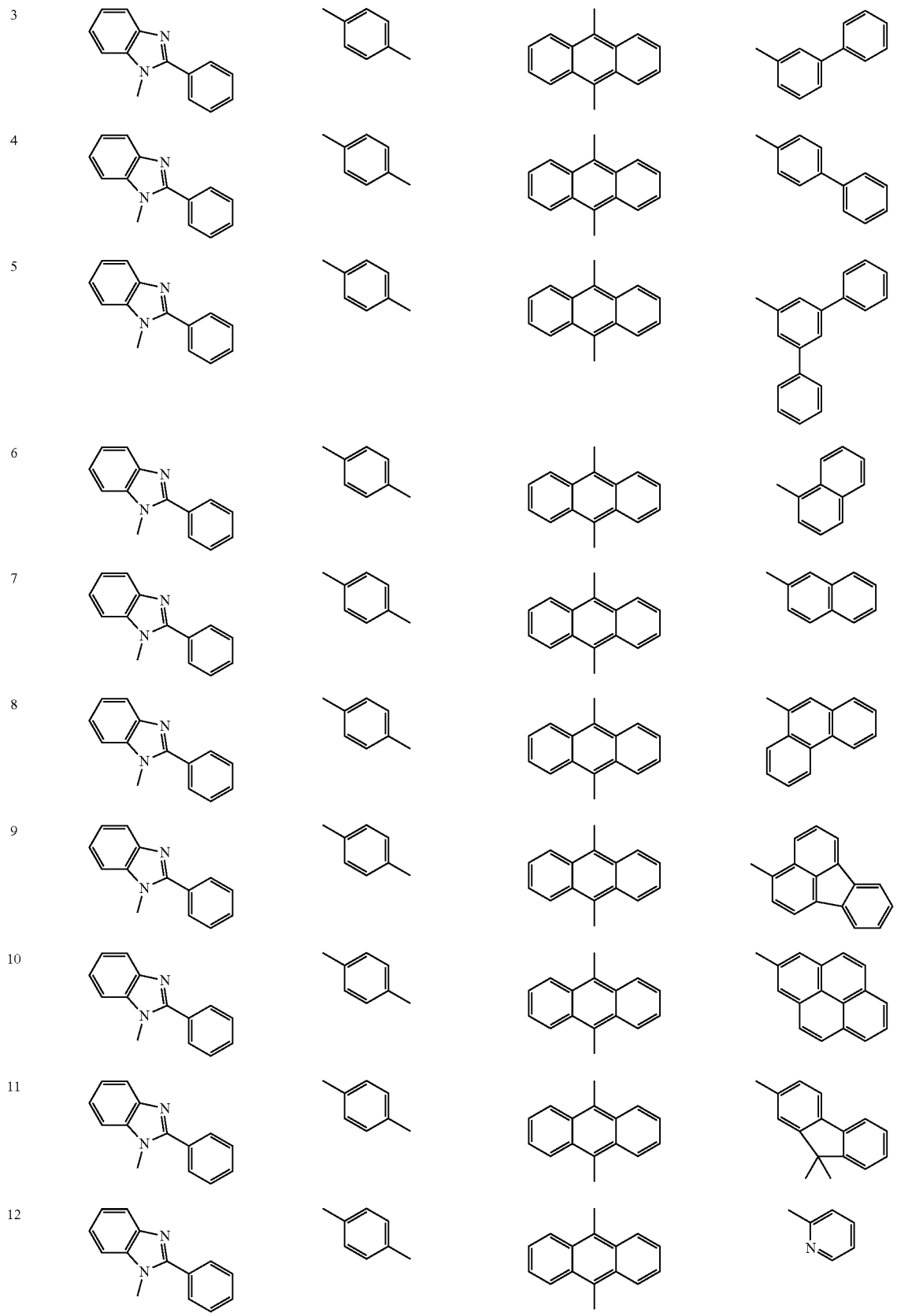

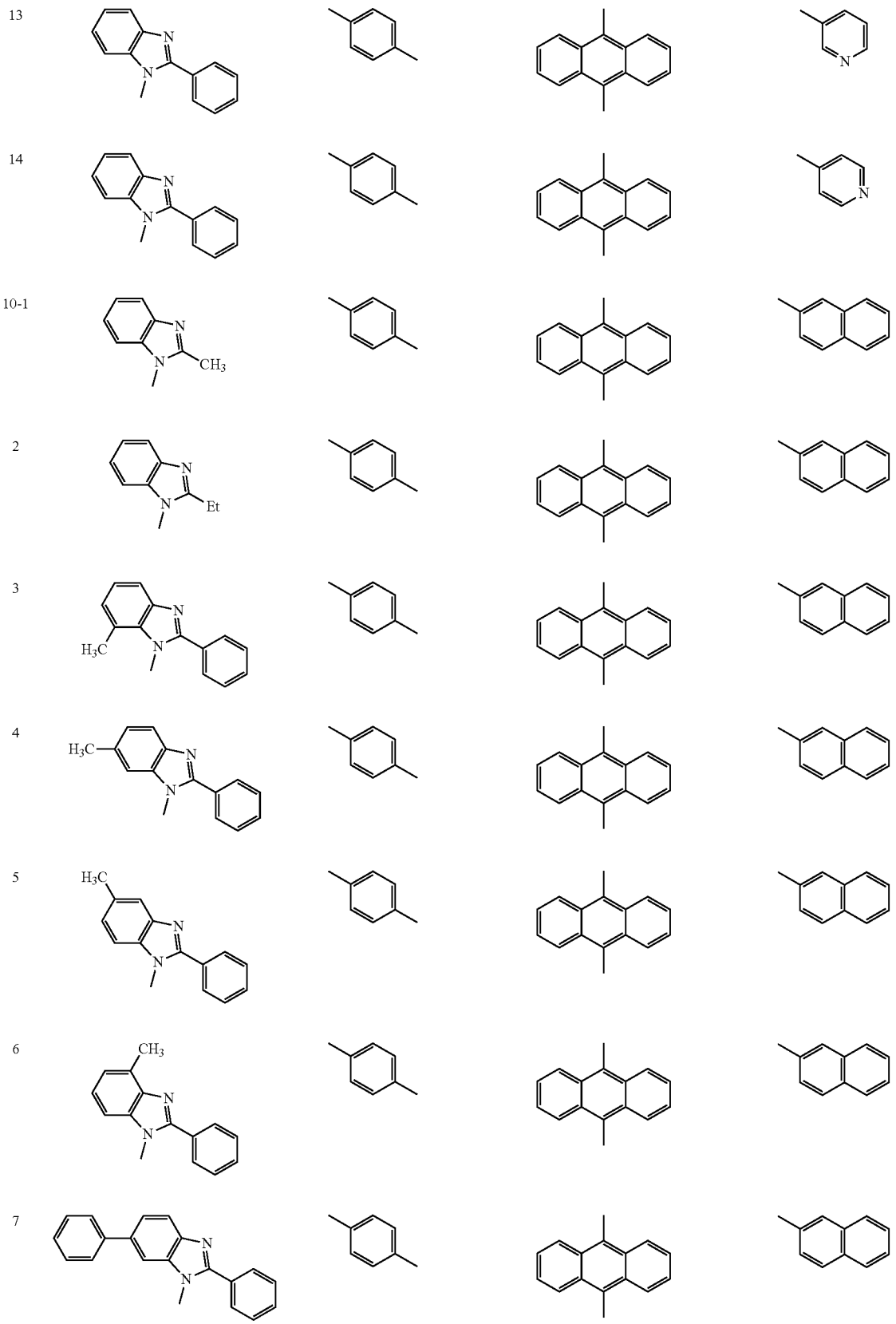

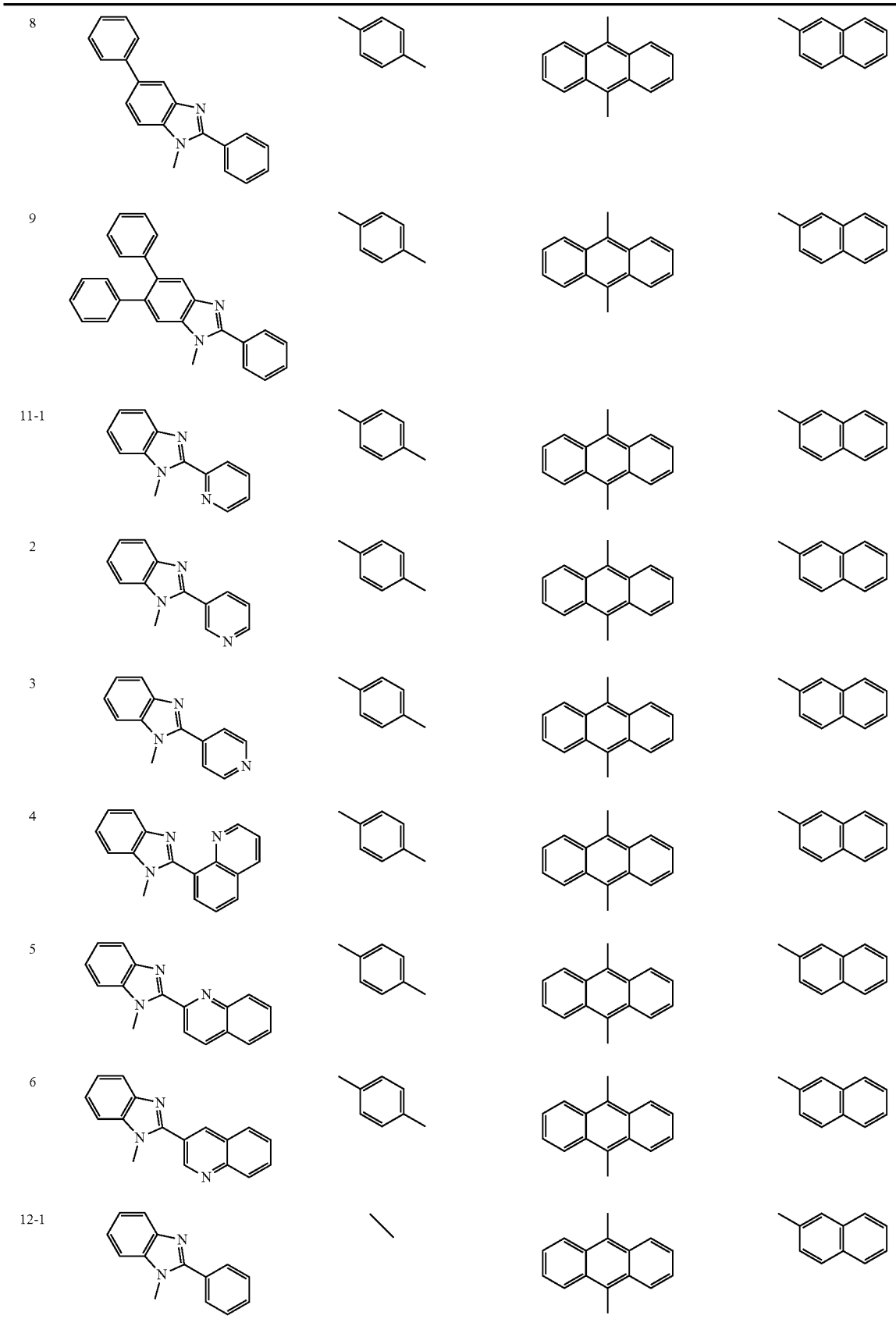

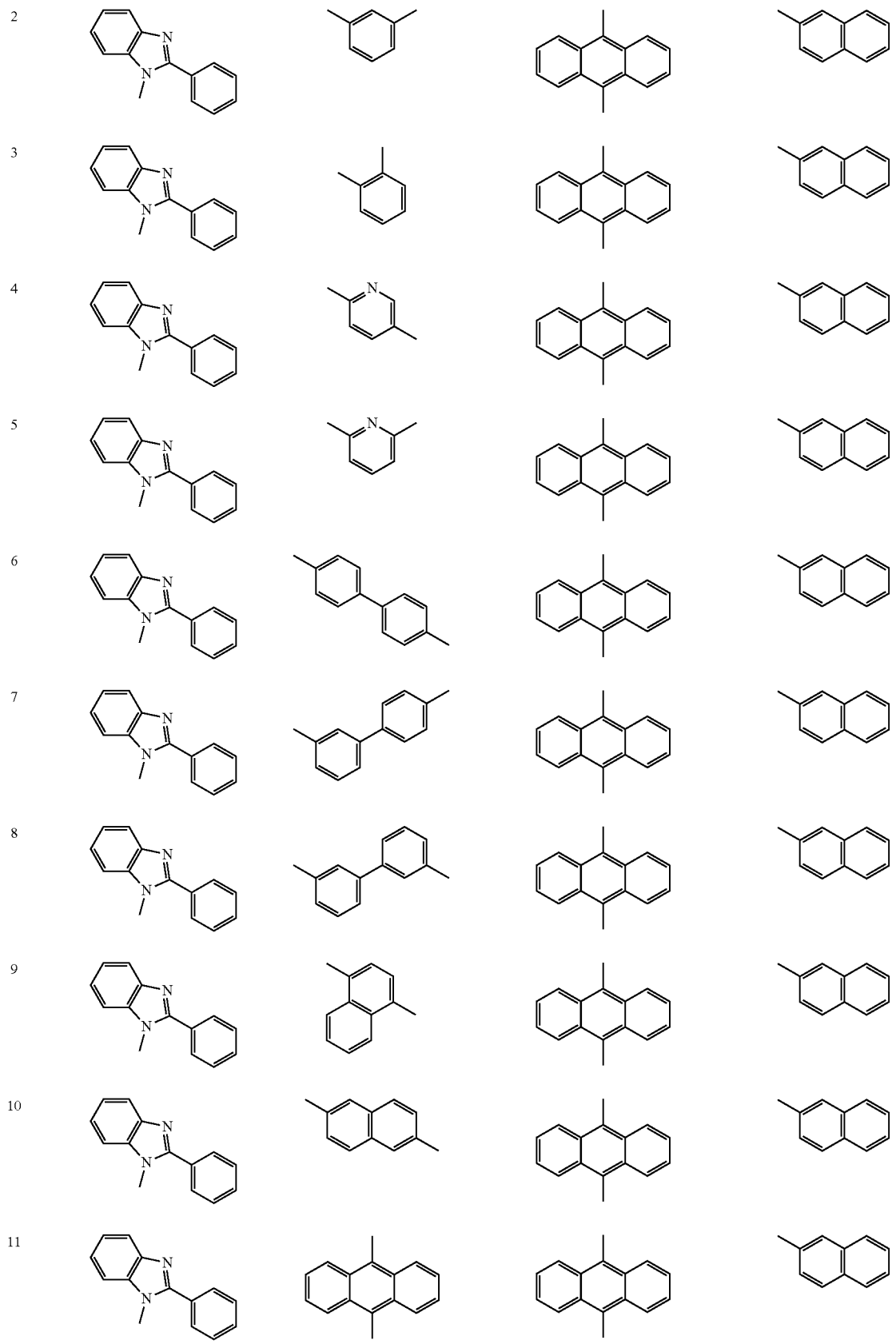

-continued
| | | | | |
|---|---|---|---|---|
| 13-1 | 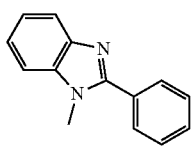 [SMILES: Cn1c(-c2ccccc2)nc2ccccc21] | 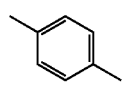 | 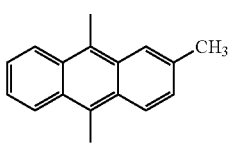 | 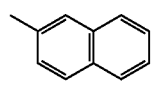 |
| 2 | 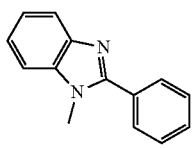 [SMILES: Cn1c(-c2ccccc2)nc2ccccc21] | 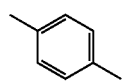 | 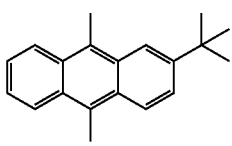 | 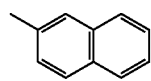 |
| 3 | 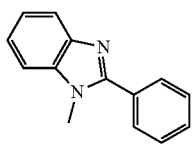 [SMILES: Cn1c(-c2ccccc2)nc2ccccc21] | 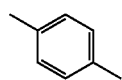 | 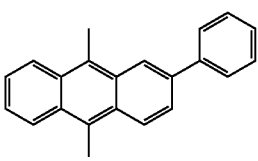 | 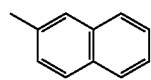 |
| 4 | 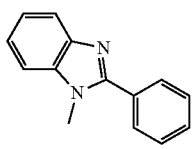 [SMILES: Cn1c(-c2ccccc2)nc2ccccc21] | 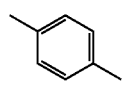 | 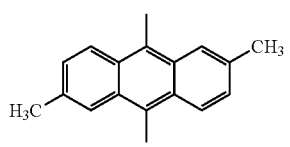 | 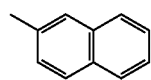 |
| 5 | 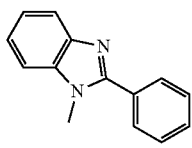 [SMILES: Cn1c(-c2ccccc2)nc2ccccc21] | 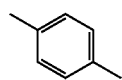 | 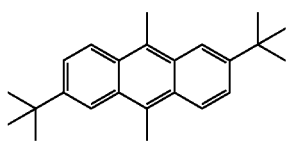 | 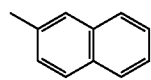 |
| 6 | 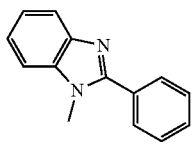 [SMILES: Cn1c(-c2ccccc2)nc2ccccc21] | 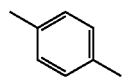 | 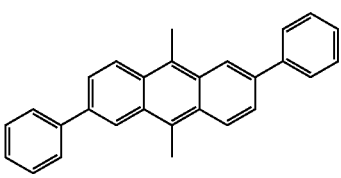 | 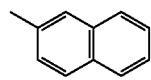 |
| 14-1 | 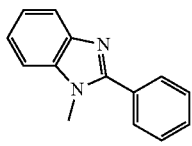 [SMILES: Cn1c(-c2ccccc2)nc2ccccc21] | 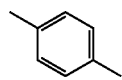 | 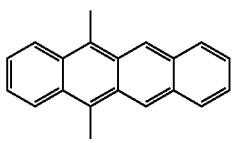 |  |
| 2 | 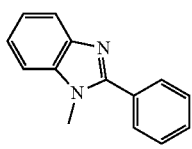 [SMILES: Cn1c(-c2ccccc2)nc2ccccc21] | 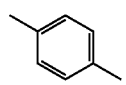 | 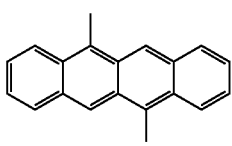 |  |
| 3 | 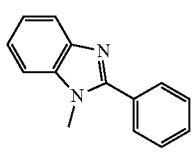 [SMILES: Cn1c(-c2ccccc2)nc2ccccc21] | 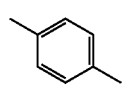 | 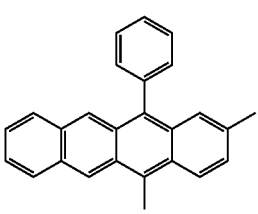 |  |

-continued
| | | L³ | Ar³ | Ar² |
|---|---|---|---|---|
| 4 | 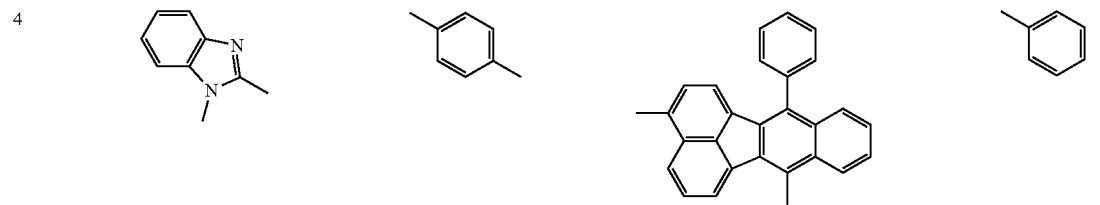 | | | |
| 5 | 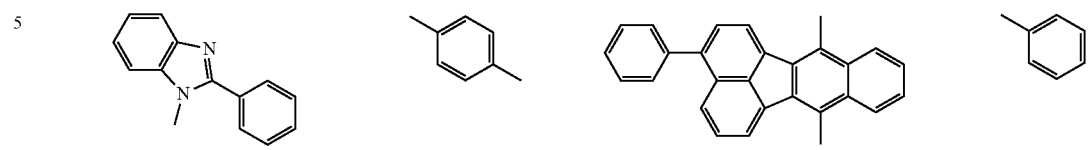 | | | |
| | | L³ | Ar³ | Ar² |
|---|---|---|---|---|
| 15-1 | 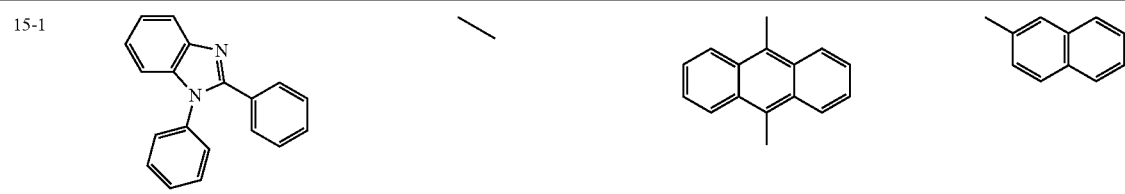 | | | |
| 2 | 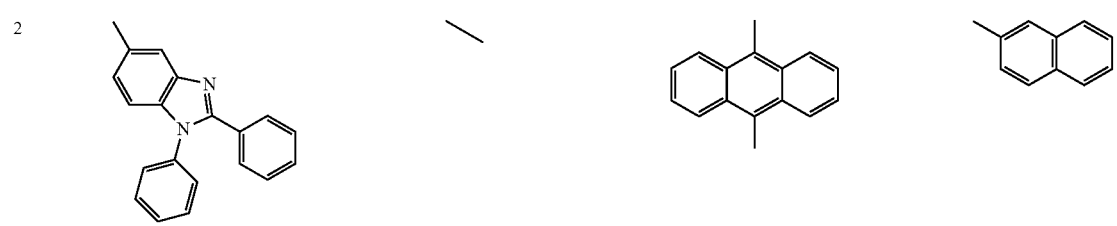 | | | |
| 3 | 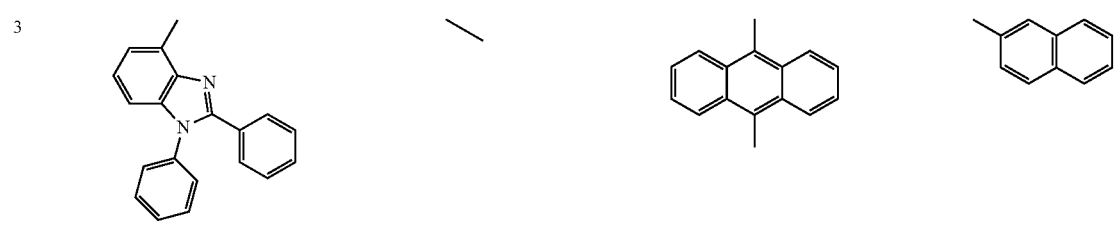 | | | |
| 4 | 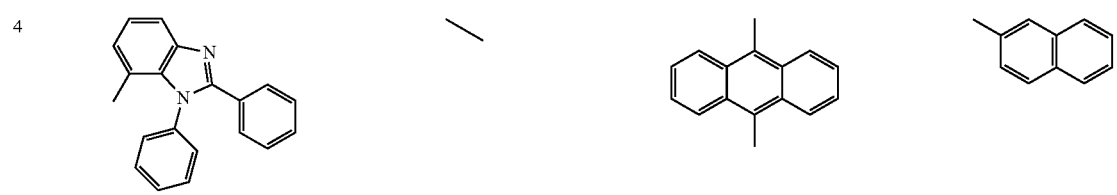 | | | |
| 5 |  | | | |

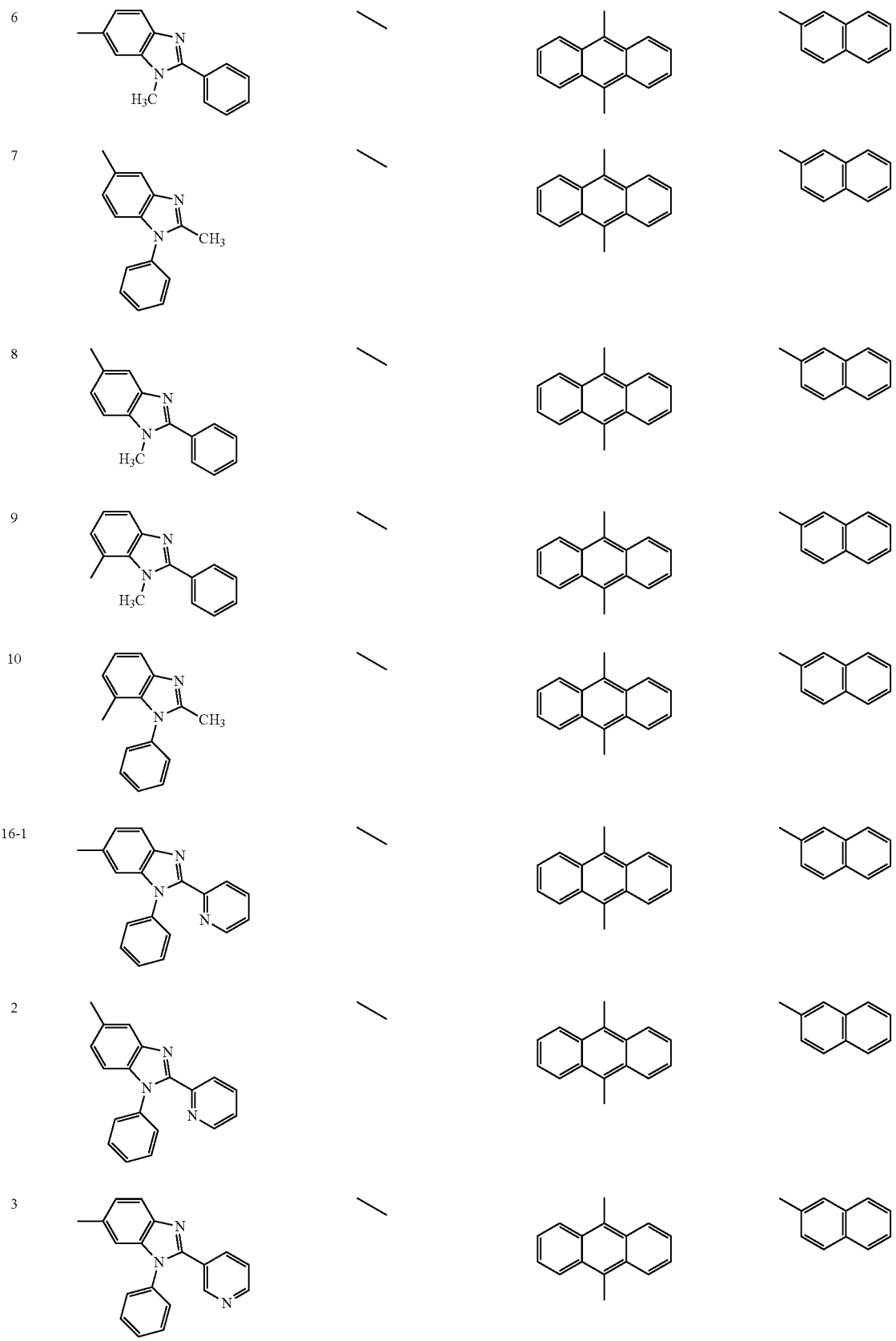

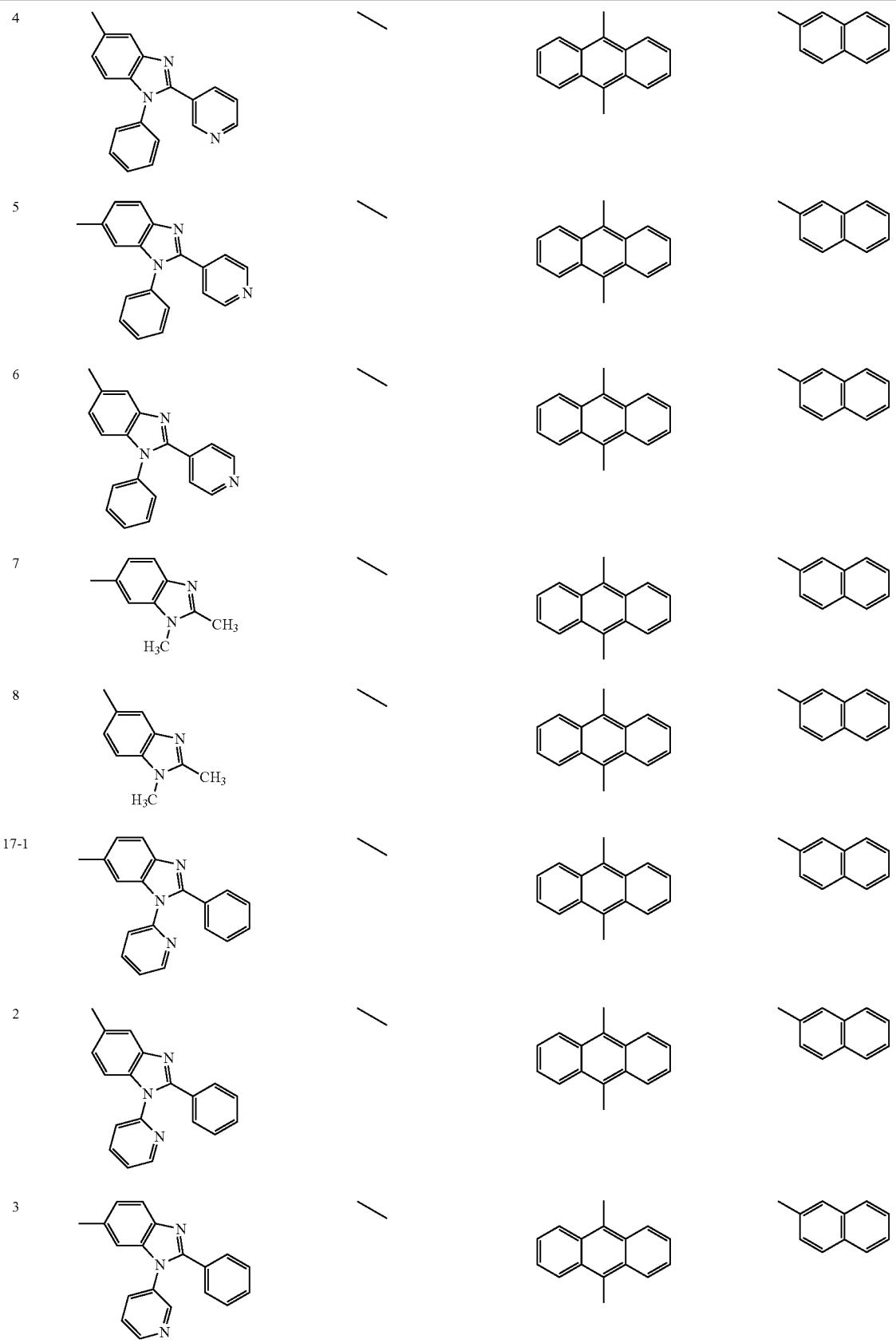

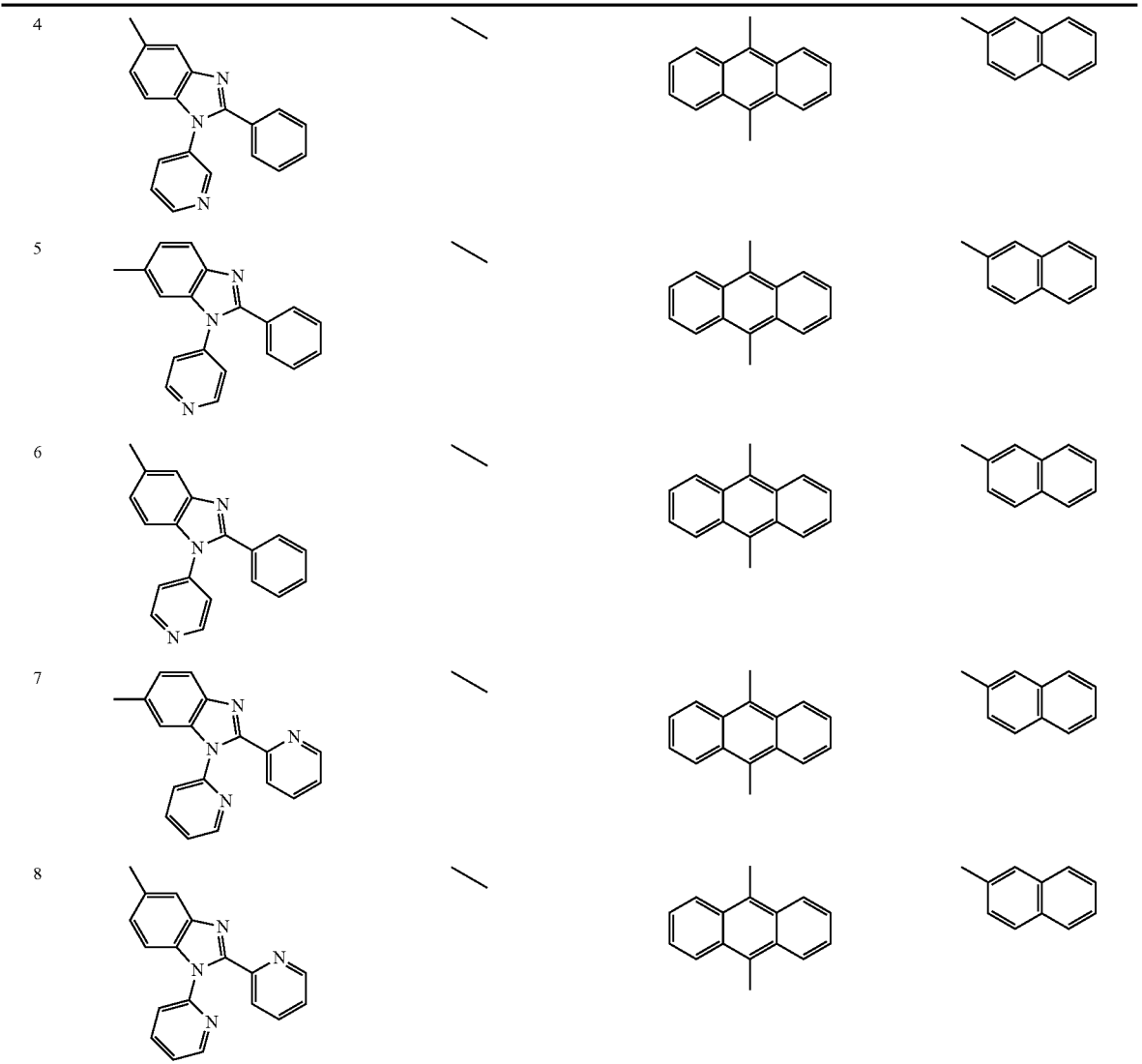

(iii) Chalcogenide

The incorporation of the chalcogenide into the "layer according to the present invention" can achieve high luminous efficiency at a low voltage.

The chalcogenide is not particularly limited and a known product can be used. A compound containing an oxygen atom, a sulfur atom, a selenium atom, or a tellurium atom can be given as an example of the chalcogenide as usual. The chalcogenide is preferably a chalcogenide containing a metal, and examples of such chalcogenide include zinc oxide, zinc sulfide, cadmium sulfide, and zinc selenide. Of those, a chalcogenide containing a metal belonging to Group 12 of the periodic table is preferred, and at least one kind selected from the group consisting of zinc oxide, zinc sulfide, and cadmium sulfide is more preferred.

It should be noted that an aluminum layer having a thickness of 0.5 to 3 nm or a layer having a thickness of 0.5 to 3 nm and formed of an alloy of magnesium and silver may exist in the "layer according to the present invention" because a driving voltage can be suppressed to a low level in the present invention even when the electron injection region is made thick. In addition, by the same reason as that described in the foregoing, the "layer according to the present invention" may be a layer obtained by mixing the oxide of the transition metal belonging to any one of Groups 5 to 8 of the periodic table, the nitrogen-containing heterocyclic derivative, or the chalcogenide, and the compound (1) with, for example, a metal or alloy having a small work function to be generally used as a cathode such as aluminum or an alloy of magnesium and silver, an electrically conductive compound, or a mixture thereof.

In general, a sputtering method is employed upon formation of an electrode layer in the tandem type device. However, the deterioration of organic matter is typically caused by generated plasma. In order that the deterioration may be prevented, the insertion of a thick electron injecting layer constructed of an inorganic compound is effective, and the formation of the electron injection region according to the above-mentioned method by which an increase in the driving voltage of the device can be prevented is also effective.

The thickness of the "layer according to the present invention," which is not particularly limited, is preferably 1 nm to 1 μm in ordinary cases, and is more preferably 1 nm to 100 nm, still more preferably 2 nm to 30 nm, particularly preferably 5 nm to 20 nm from the viewpoint of the realization of good electron transporting property.

In addition, the thickness of the electron injection region, which is not particularly limited, is preferably 1 nm to 1 μm in ordinary cases.

(Any Other Electron Injecting or Transporting Layer)

The electron injection region may be constructed by laminating any other electron injecting layer or electron transporting layer as well as the layer according to the present invention. The electron injecting or transporting layer is a layer that aids the injection of an electron into the light emitting layer, and the layer has a large electron mobility.

A material to be used in an electron transporting layer of an ordinary organic EL device can be used as a material to be used in the electron transporting layer. Suitable examples of the material include a metal complex of 8-hydroxyquinoline or of a derivative thereof, an oxadiazole derivative, and a nitrogen-containing heterocyclic derivative. A metal chelate oxinoid compound containing a chelate of an oxine (generally 8-quinolinol or 8-hydroxyquinoline) such as tris(8-quinolinol)aluminum can be given as a specific example of the metal complex of 8-hydroxyquinoline or of the derivative thereof.

The nitrogen-containing heterocyclic derivative is, for example, a benzoimidazole derivative represented by the above-mentioned general formula (A) or (B).

Thicknesses and methods to be typically employed for an organic EL device have only to be adopted as the thicknesses of, and formation methods for, those layers.

The electron injecting layer and the electron transporting layer may each contain, in addition to the above-mentioned compounds, a phosphine oxide compound (see JP 2004-203828A) and a phenanthroline derivative (see JP 05-331459 A, JP 07-82551 A, JP 10-79297 A, JP 2001-267080 A, and JP 2001-131174 A).

<Anode Layer>

A known material that has been used as an anode material for an organic EL device can be used without any particular limitation as an anode material to be used in the organic EL device of the present invention.

Examples of the anode material include indium tin oxide alloys (ITO), tin oxide (NESA), gold, silver, platinum, and copper. The anode layer serves to inject a hole into a hole transporting layer or the light emitting layer, and the anode material, which is not particularly limited, preferably has a work function of 4.5 eV or more.

<Hole Injecting Layer and Hole Transporting Layer>

When a hole injecting layer or hole transporting layer (a hole injecting/transporting layer is also permitted) is provided, a known material that has been used as a material for a hole injecting layer or hole transporting layer of an organic EL device can be used without any particular limitation as a material for any such layer. It should be noted that the following compound is preferred as a material for the hole injecting layer or hole transporting layer. The compound has an ability to transport a hole, has a hole injecting effect from the anode layer and an excellent hole injecting effect on the light emitting layer or a light emitting material, prevents the transfer of an exciton generated in the light emitting layer to the electron injecting layer or an electron injecting material, and is excellent in ability to form a thin film.

Examples of the material for the hole injecting layer or hole transporting layer include, but are not particularly limited to, a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acyl-hydrazone, polyarylalkane, stilbene, butadiene, and derivatives thereof, amine derivatives such as benzidine type triphenylamine, styrylamine type triphenylamine, diamine type triphenylamine, and polymer materials such as polyvinyl carbazole, polysilane, and a conductive polymer.

<Light Emitting Layer>

A known light emitting material or doping material that has been used as a material for a light emitting layer of an organic EL device can be used without any particular limitation in the light emitting layer. When a doping material is used in combination, emission luminance and luminous efficiency are improved, and even red or blue light emission can be obtained.

Examples of a host material or a doping material include: polyfused aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethinyl)anthracene, and 1,4-bis(9'-ethinylanthracenyl)benzene and derivatives thereof; organic metal complexes such as tris(8-quinolinolato) aluminum and bis-(2-methyl-8-quinolinolato)-4-(phenylphenolato)aluminum; a triarylamine derivative; a styrylamine derivative; a stilbene derivative; a coumarin derivative; a pyrane derivative; an oxazone derivative; a benzothiazole derivative; a benzoxazole derivative; a benzimidazole derivative; a pyrazine derivative; a cinnamate derivative; a diketopyrrolopyrrole derivative; an acridone derivative; and a quinacridone derivative, but the material is not particularly limited thereto.

<Cathode Layer>

A known material that has been used as a cathode material for an organic EL device can be used without any particular limitation as an cathode material to be used in the organic EL device of the present invention.

In addition, as the cathode layer, a material having a small work function is preferred in view to inject an electron into an electron injecting layer or a light emitting layer. Specifically, indium, aluminum, magnesium, an magnesium-indium alloy, a magnesium-aluminum alloy, an aluminum-lithium alloy, an aluminum-scandium-lithium alloy, and a magnesium-silver alloy may be preferably used. Further, oxide semiconductors such as indium tin oxide and indium zinc oxide may also be preferably used.

<Protective Layer>

Further, a protective layer that protects the organic EL device from, for example, moisture in the air may be provided. Providing the protective layer can suppress deterioration resulting from a dark spot generated in the organic EL device.

A material for the protective layer is preferably, for example, SiN, SiON, $SiO_2$, or $Al_2O_3$ from the viewpoint of the suppression of the dark spot.

When the protective layer is provided, its thickness, which is not particularly limited, is preferably 100 to 5,000 nm in ordinary cases.

A method of forming each layer of the organic EL device is not particularly limited, and a known method based on a deposition method such as a vacuum deposition method of, for example, a resistance heating type, electron beam type, high-frequency induction type, or laser type or the sputtering method, or on an application method such as a dipping method, spin coating method, casting method, bar coating method, or roll coating method involving applying a solution prepared by dissolving a material for each layer in a solvent can be employed.

It should be noted that the cathode layer is generally formed by a resistance heating method when magnesium, aluminum, a magnesium-silver alloy, or the like is used as a cathode material. In addition, the cathode layer is generally formed by the sputtering method when an oxide semiconductor such as an indium tin oxide or an indium zinc oxide is used as a cathode material.

In particular, when the electron injection region is formed of the compound (1) and the oxide of the transition metal belonging to any one of Groups 5 to 8 of the periodic table in an embodiment of the present application, the electron injection region has high sputtering resistance. Therefore, when an oxide semiconductor such as an indium tin oxide or an indium zinc oxide is used as a cathode material, the electron injection region (the layer contacting the cathode layer when the region is formed of a plurality of layers) is preferably formed of the compound (1) and the oxide of the transition metal belonging to any one of Groups 5 to 8 of the periodic table.

<Intermediate Conductive Layer>

The organic EL device of the present application may further have one or more intermediate conductive layers between the two electrode layers. In this case, the device may have a light emitting layer between an electrode layer and an intermediate conductive layer and/or between intermediate conductive layers when a plurality of intermediate conductive layers exist, and may further have an electron injection region formed of one or two or more layers between the light emitting layer and the cathode layer and/or between the light emitting layer and an intermediate conductive layer.

When an intermediate conductive layer is provided, a material to be used in the intermediate conductive layer of the organic EL device is not particularly limited as long as the material generates a hole and an electron and injects the generated hole or electron to an adjacent layer on the side of an opposing electrode (the anode layer or the cathode layer), and a known material can be used. A material described in, for example, JP 2003-045676 A or JP 11-329748 A can be utilized as a material for the intermediate conductive layer to be used between the two electrode layers.

As in the cathode layer, the intermediate conductive layer is generally formed by the resistance heating method when magnesium, aluminum, a magnesium-silver alloy, or the like is used as a material for the layer. In addition, the layer is generally formed by the sputtering method when an oxide semiconductor such as an indium tin oxide or an indium zinc oxide is used.

Therefore, as in the case of the cathode layer, when an oxide semiconductor such as an indium tin oxide or an indium zinc oxide is used as a material for the intermediate conductive layer, the electron injection region (the layer contacting the intermediate conductive layer when the region is formed of a plurality of layers) is preferably formed of the compound (1) and the oxide of the transition metal belonging to any one of Groups 5 to 8 of the periodic table from the viewpoint of sputtering resistance.

When an oxide semiconductor such as an indium tin oxide or an indium zinc oxide is used in the intermediate conductive layer in such an embodiment that an Al layer or the like is included in the electron injection region, an influence of sputtering acts on the electron injection region even in the case where Al is laminated in a region contacting the cathode layer. Accordingly, the layer contacting the intermediate conductive layer out of the electron injection region is particularly preferably formed of the compound (1) and the oxide of the transition metal belonging to any one of Groups 5 to 8 of the periodic table.

In ordinary cases, the thickness of each layer except the electron injection region in the organic EL device of the present invention preferably falls within the range of 1 nm to 1 µm because too small a thickness is generally apt to cause a defect such as a pinhole, and in contrast, too large a thickness generally requires a high applied voltage, thereby resulting in poor efficiency. However, the thickness is not particularly limited to the range.

EXAMPLES

Hereinafter, the present invention is described in detail by way of examples. However, the present invention is by no means limited to these examples.

Example 1

A glass substrate with an ITO transparent electrode having a size of 25 mm by 75 mm by 1.1 mm thick (manufactured by ASAHI GLASS CO., LTD.) was subjected to ultrasonic cleaning in isopropyl alcohol for 5 minutes. After that, the substrate was subjected to UV ozone cleaning for 30 minutes.

The glass substrate with the transparent electrode line after the cleaning was mounted on a substrate holder of a vacuum deposition device. First, the following compound (HI) was formed into a film having a thickness of 60 nm by resistance heating deposition on the surface on the side where the transparent electrode line was formed so as to cover the transparent electrode. The film of the compound (HI) functions as a hole injecting layer.

Next, the following compound (HT) was formed into a film on the HI film by resistance heating deposition so as to have a thickness of 20 nm. Thus, a hole transporting layer was formed.

Further, the following host compound (H1) and the following dopant compound (D1) were formed into a film on the HT film by resistance heating deposition (co-deposition) so as to have a thickness of 40 nm. Thus, a light emitting layer was obtained. At this time, the concentration of the dopant compound (D1) was set to 10 weight %.

Next, the following compound (ET) was formed into a film on the light emitting layer by resistance heating deposition so as to have a thickness of 17.5 nm. The ET film functions as an electron transporting layer.

Tungsten oxide and lithium metasilicate were formed into a film at a weight ratio of 1:4 on the ET film by resistance heating deposition (co-deposition) so as to have a thickness of 2.5 nm. Thus, an electron injecting layer was formed.

Metal aluminum (Al) was formed into a film on the electron injecting layer by resistance heating deposition so as to have a thickness of 100 nm. Thus, a cathode layer was formed. As a result of the foregoing, an organic EL device was produced.

The driving voltage and current efficiency (luminous efficiency) of the resultant organic EL device at a current density of 10.0 mA/cm$^2$ were measured. Further, its half lifetime was measured by performing a DC continuous energization test at an initial luminance of 1,000 cd/m$^2$ and room temperature. Table 1 shows the results.

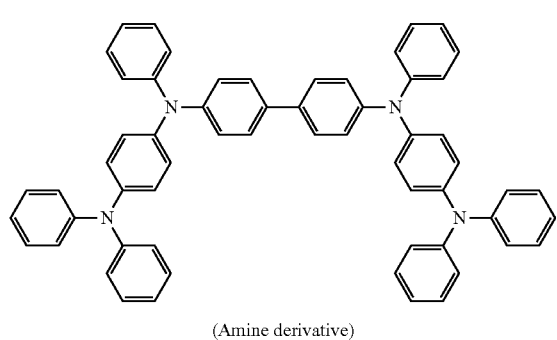

HI
(Amine derivative)

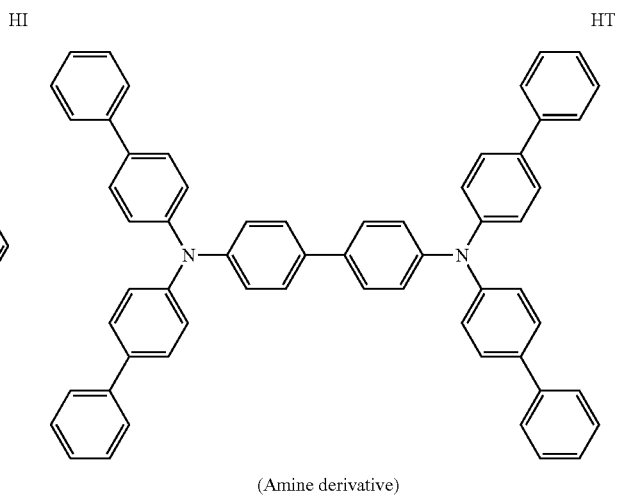

HT
(Amine derivative)

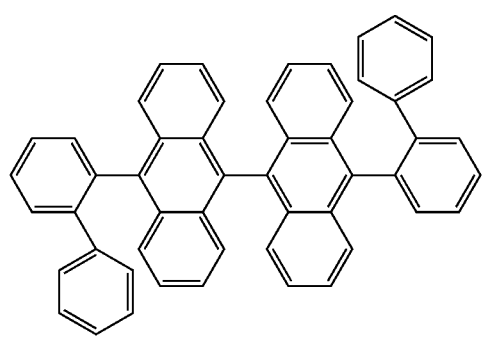

H1
(Anthracene derivative)

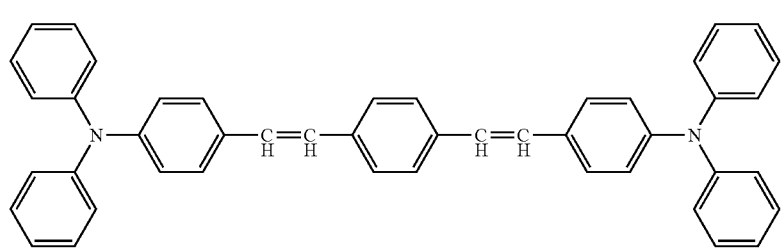

D1
(Styrylamine type triphenylamine)

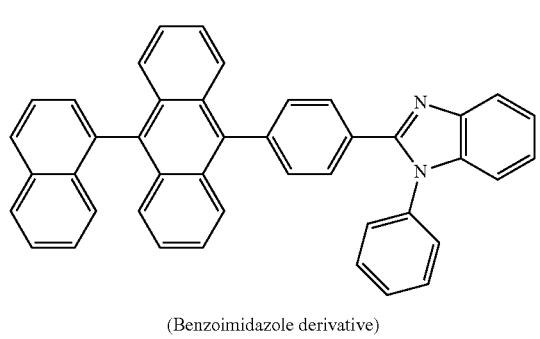

ET
(Benzoimidazole derivative)

Example 2

An organic EL device was produced in the same manner as in Example 1 except that molybdenum oxide and lithium metasilicate (at a weight ratio of 1:4) were used instead of tungsten oxide and lithium metasilicate (at a weight ratio of 1:4) upon formation of the electron injecting layer in Example 1.

Table 1 shows the results of the respective measurements conducted on the resultant organic EL device in the same manner as in Example 1.

Example 3

An organic EL device was produced in the same manner as in Example 1 except that tungsten oxide and cesium metasilicate (at a weight ratio of 1:4) were used instead of tungsten oxide and lithium metasilicate (at a weight ratio of 1:4) upon formation of the electron injecting layer in Example 1.

Table 1 shows the results of the respective measurements conducted on the resultant organic EL device in the same manner as in Example 1.

Example 4

An organic EL device was produced in the same manner as in Example 1 except that tungsten oxide and potassium metasilicate (at a weight ratio of 1:4) were used instead of tungsten oxide and lithium metasilicate (at a weight ratio of 1:4) upon formation of the electron injecting layer in Example 1.

Table 1 shows the results of the respective measurements conducted on the resultant organic EL device in the same manner as in Example 1.

Example 5

An organic EL device was produced in the same manner as in Example 1 except that molybdenum oxide and cesium metasilicate (at a weight ratio of 1:4) were used instead of tungsten oxide and lithium metasilicate (at a weight ratio of 1:4) upon formation of the electron injecting layer in Example 1.

Table 1 shows the results of the respective measurements conducted on the resultant organic EL device in the same manner as in Example 1.

Example 6

An organic EL device was produced in the same manner as in Example 1 except that the usage ratio between tungsten oxide and lithium metasilicate upon formation of the electron injecting layer in Example 1 was set to a weight ratio of 1:9 instead of a weight ratio of 1:4.

Table 1 shows the results of the respective measurements conducted on the resultant organic EL device in the same manner as in Example 1.

Example 7

An organic EL device was produced in the same manner as in Example 1 except that the ratio between tungsten oxide and lithium metasilicate upon formation of the electron injecting layer in Example 1 was set to a weight ratio of 1:1 instead of a weight ratio of 1:4.

Table 1 shows the results of the respective measurements conducted on the resultant organic EL device in the same manner as in Example 1.

Example 8

A series of film formations ending on the formation of a light emitting layer was performed in the same manner as in Example 1. After that, the above-mentioned compound (ET) was formed into a film on the light emitting layer by resistance heating deposition so as to have a thickness of 15 nm. The ET film functions as an electron transporting layer.

Tungsten oxide and lithium metasilicate were formed into a film at a weight ratio of 1:4 on the ET film by resistance heating deposition (co-deposition) so as to have a thickness of 2.5 nm. Aluminum (Al) was formed into a film on the film by resistance heating deposition so as to have a thickness of 2 nm. Further, tungsten oxide and lithium metasilicate were formed into a film at a weight ratio of 1:4 on the Al film by resistance heating deposition (co-deposition) so as to have a thickness of 2.5 nm. Those films function as an electron injecting layer.

Aluminum (Al) was formed into a film on the electron injecting layer by resistance heating deposition so as to have a thickness of 100 nm. Thus, a cathode layer was formed. As a result of the foregoing, an organic EL device was produced.

Table 1 shows the results of the respective measurements conducted on the resultant organic EL device in the same manner as in Example 1.

Example 9

An organic EL device was produced in the same manner as in Example 1 except that ET and lithium metasilicate (at a weight ratio of 1:1) were used instead of tungsten oxide and lithium metasilicate (at a weight ratio of 1:4) upon formation of the electron injecting layer in Example 1.

Table 1 shows the results of the respective measurements conducted on the resultant organic EL device in the same manner as in Example 1.

Example 10

An organic EL device was produced in the same manner as in Example 1 except that zinc sulfide (ZnS) as a chalcogenide and lithium metasilicate (at a weight ratio of 1:1) were used instead of tungsten oxide and lithium metasilicate (at a weight ratio of 1:4) upon formation of the electron injecting layer in Example 1.

Table 1 shows the results of the respective measurements conducted on the resultant organic EL device in the same manner as in Example 1.

Comparative Example 1

An organic EL device was produced in the same manner as in Example 1 except that tungsten oxide and lithium oxide (at a weight ratio of 1:4) were used instead of tungsten oxide and lithium metasilicate (at a weight ratio of 1:4) upon formation of the electron injecting layer in Example 1.

Table 1 shows the results of the respective measurements conducted on the resultant organic EL device in the same manner as in Example 1.

Comparative Example 2

An organic EL device was produced in the same manner as in Example 1 except that tungsten oxide and lithium fluoride (at a weight ratio of 1:4) were used instead of tungsten oxide and lithium metasilicate (at a weight ratio of 1:4) upon formation of the electron injecting layer in Example 1.

Table 1 shows the results of the respective measurements conducted on the resultant organic EL device in the same manner as in Example 1.

Comparative Example 3

An organic EL device was produced in the same manner as in Example 1 except that only lithium metasilicate was formed into a film having a thickness of 2.5 nm instead of tungsten oxide and lithium metasilicate (at a weight ratio of 1:4) upon formation of the electron injecting layer in Example 1.

Table 1 shows the results of the respective measurements conducted on the resultant organic EL device in the same manner as in Example 1.

Comparative Example 4

An organic EL device was produced in the same manner as in Example 1 except that a tungsten oxide film having a thickness of 2.5 nm and a potassium metasilicate film having a thickness of 0.5 nm were laminated (provided that the tungsten oxide film was on the light emitting layer side) instead of the co-deposition of tungsten oxide and lithium metasilicate (at a weight ratio of 1:4) upon formation of the electron injecting layer in Example 1.

Table 1 shows the results of the respective measurements conducted on the resultant organic EL device in the same manner as in Example 1.

TABLE 1

|  | Current density (mA/cm$^2$) | Driving voltage (V) | Current efficiency (cd/A) | Half lifetime (hour(s)) |
| --- | --- | --- | --- | --- |
| Example 1 | 10.0 | 5.9 | 9.24 | 6,500 |
| Example 2 | 10.0 | 6.2 | 8.99 | 9,800 |
| Example 3 | 10.0 | 5.4 | 7.54 | 5,100 |
| Example 4 | 10.0 | 5.5 | 8.02 | 5,600 |
| Example 5 | 10.0 | 5.4 | 8.28 | 6,200 |
| Example 6 | 10.0 | 6.3 | 8.65 | 5,300 |
| Example 7 | 10.0 | 7.0 | 6.28 | 6,700 |
| Example 8 | 10.0 | 5.6 | 8.16 | 12,000 |
| Example 9 | 10.0 | 6.3 | 6.55 | 7,200 |
| Example 10 | 10.0 | 7.2 | 5.98 | 5,400 |
| Comparative Example 1 | 10.0 | 6.4 | 1.68 | 2,300 |
| Comparative Example 2 | 10.0 | 7.2 | 6.0 | 150 |
| Comparative Example 3 | 10.0 | 15.0 | 2.23 | 30 |
| Comparative Example 4 | 10.0 | 8.5 | 5.62 | 600 |

As can be seen from Table 1, in the organic EL device of the present invention (see Examples 1 to 10), the driving voltage is relatively low at the same current density. In other words, the present invention has succeeded in improving the efficiency with which an electron is injected from the cathode layer to the light emitting layer while using a thermally and chemically stable material in the electron injection region. Accordingly, the acquisition of high current efficiency at a low voltage was attained. Further, it is found that the production of an organic EL device capable of maintaining a long lifetime was attained.

On the other hand, in the case of the organic EL device whose electron injection region did not contain the compound (1) (see Comparative Examples 1 and 2), the electron injection efficiency reduced, the driving voltage at the same current density increased, the current efficiency reduced, and the half lifetime also reduced as compared with the organic EL device of the present invention.

In addition, when only a thick film of the compound (1) was laminated in the electron injection region (see Comparative Example 3), owing to high insulating property of the material, the device was driven at an extremely high voltage, its current efficiency reduced, and its half lifetime was extremely short. Further, when the respective layers of the compound (1) and the transition metal oxide were laminated in the electron injection region without being co-deposited, the device was driven at a high voltage, its current efficiency reduced, and its half lifetime was short (see Comparative Example 4).

Industrial Applicability

The organic EL device of the present invention is thermally and chemically stable, has high electron injection efficiency, provides high luminous efficiency at a low voltage, and can maintain a long lifetime. In addition, the electron injection region of the organic EL device of the present invention can function as a sputtering damage reducing layer.

Accordingly, the organic EL device of the present invention is extremely useful as, for example, a full-color display, an information display unit, an on-vehicle display unit, or a lighting apparatus.

The invention claimed is:

1. An organic electroluminescence device, comprising:
two electrode layers;
optionally, at least one intermediate conductive layer;
a light emitting layer; and
an electron injection region,
wherein the light emitting layer is between at least one selected from the group consisting of the two electrode layers, the electrode layer and the at least one optional intermediate conductive layer and two optional intermediate conductive layers,
wherein the electron injection region comprises at least one layer between at least one selected from the group consisting of the light emitting layer and a cathode layer and the light emitting layer and the at least one optional intermediate conductive layer,
wherein at least one layer in the electron injection region comprises at least one selected from the group consisting of an oxide of a transition metal belonging to any one of Groups 5 to 8 of the periodic table, a nitrogen-comprising heterocyclic compound, and a chalcogenide, and further comprises a compound represented by the following general formula (1):

$$MxAOy \qquad (1)$$

wherein
M is Li, Na, K, Rb, or Cs;
A is Zr, V, Nb, Ta, Si, or Ge;
x is an integer of 1 or 2; and
y is an integer of 1 to 4.

2. The device of claim 1, wherein the at least one layer in the electron injection region is formed by a co-deposition method.

3. The device of claim 1, wherein the at least one layer in the electron injection region contacts one of the two electrode layers or the at least one optional intermediate conductive layer.

4. The device of claim 1, wherein A in the compound (1) is Si or Ge.

5. The device of claim 1, wherein A in the compound (1) is Si.

6. The device of claim 1, wherein a content of the compound (1) in the at least one layer in the electron injection region is 5 to 90 weight %.

7. The device of claim 1, wherein a content of the compound (1) in the at least one layer in the electron injection region is 50 to 90 weight %.

8. The device of claim 1, wherein M in the compound (1) is Li or Na.

9. The device of claim 1, wherein the electron injection region comprises the oxide of the transition metal belonging to any one of Groups 5 to 8 of the periodic table and the compound (1).

10. The device of claim 1, wherein the electron injection region comprises the nitrogen-comprising heterocyclic compound and the compound (1).

11. The device of claim 1, wherein the electron injection region comprises the chalcogenide and the compound (1).

12. The device of claim 1, wherein the oxide of the transition metal belonging to any one of Groups 5 to 8 of the periodic table comprises an oxide of at least one selected from the group consisting of V, Nb, Ta, Mo, W, Re, and Ru.

13. The device of claim 1, wherein the oxide of the transition metal belonging to any one of Groups 5 to 8 of the periodic table comprises an oxide of at least one metal selected from the group consisting of Mo and W.

14. The device of claim 1, wherein the nitrogen-comprising heterocyclic compound comprises a benzoimidazole compound represented by the following general formula (A) or (B):

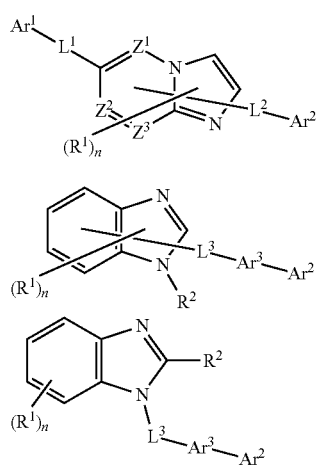

wherein:

$Z^1$, $Z^2$, and $Z^3$ each independently is a nitrogen atom or a carbon atom;

$R^1$ and $R^2$ each independently is a substituted or unsubstituted aryl group comprising 6 to 60 carbon atoms, a substituted or unsubstituted heteroaryl group comprising 3 to 60 carbon atoms, an alkyl group comprising 1 to 20 carbon atoms, a halogen atom-substituted alkyl group comprising 1 to 20 carbon atoms, or an alkoxy group comprising 1 to 20 carbon atoms;

n is an integer of 0 to 5, wherein when n is an integer of 2 or more, a plurality of $R^1$'s may be identical to or different from each other, and a plurality of $R^1$'s adjacent to each other may be bonded to each other to form a substituted or unsubstituted, aromatic hydrocarbon ring;

$Ar^1$ is a substituted or unsubstituted aryl group comprising 6 to 60 carbon atoms, or a substituted or unsubstituted heteroaryl group comprising 3 to 60 carbon atoms;

$Ar^2$ is a hydrogen atom, an alkyl group comprising 1 to 20 carbon atoms, a halogen atom-substituted alkyl group comprising 1 to 20 carbon atoms, an alkoxy group comprising 1 to 20 carbon atoms, a substituted or unsubstituted aryl group comprising 6 to 60 carbon atoms, or a substituted or unsubstituted heteroaryl group comprising 3 to 60 carbon atoms, wherein one of $Ar^1$ and $Ar^2$ is a substituted or unsubstituted fused ring group comprising 10 to 60 carbon atoms, or a substituted or unsubstituted, heterocyclic fused ring group comprising 9 to 60 ring forming atoms;

$Ar^3$ is a substituted or unsubstituted arylene group comprising 6 to 60 carbon atoms, or a substituted or unsubstituted heteroarylene group comprising 3 to 60 carbon atoms; and $L^1$, $L^2$, and $L^3$ each independently is a single bond, a substituted or unsubstituted arylene group comprising 6 to 60 carbon atoms, a substituted or unsubstituted, heterocyclic fused ring group comprising 9 to 60 ring forming atoms, or a substituted or unsubstituted fluorenylene group.

15. The device of claim 1, wherein the chalcogenide comprises at least one selected from the group consisting of zinc oxide, zinc sulfide, zinc selenide, and cadmium sulfide.

16. The device of claim 1, wherein the electron injection region comprises aluminum or a layer thereof.

17. The device of claim 1, wherein the electron injection region comprises an alloy of magnesium and silver or a layer thereof.

18. The device of claim 1, wherein the electron injection region has a thickness of 5 to 20 nm.

19. The device of claim 1, wherein the two electrode layers each comprise, or the at least one optional intermediate conductive layer comprises, an oxide semiconductor by a sputtering method.

* * * * *